US010201267B2

(12) United States Patent
Lieberman et al.

(10) Patent No.: US 10,201,267 B2
(45) Date of Patent: Feb. 12, 2019

(54) METHODS AND APPARATUS FOR FACILITATING DIRECT VISUALIZED RHIZOTOMY

(71) Applicant: Phoenix Spine Holdings, Inc., Phoenix, AZ (US)

(72) Inventors: Daniel Lieberman, Phoenix, AZ (US); Yani Deros, Phoenix, AZ (US); Matthew James Ibarra, Lakewood, CA (US); Kirsten Rutherford, Tempe, AZ (US); John B. Kinnard, San Tan Valley, AZ (US); Craig C. Ovans, Chandler, AZ (US)

(73) Assignee: Phoenix Spine Holdings, Inc., Phoenix, AZ (US)

( * ) Notice: Subject to any disclaimer, the term of this patent is extended or adjusted under 35 U.S.C. 154(b) by 0 days.

(21) Appl. No.: 15/163,619

(22) Filed: May 24, 2016

(65) Prior Publication Data
US 2017/0340194 A1    Nov. 30, 2017

(51) Int. Cl.
*A61B 1/00*    (2006.01)
*A61B 1/05*    (2006.01)
(Continued)

(52) U.S. Cl.
CPC ............ *A61B 1/05* (2013.01); *A61B 1/00045* (2013.01); *A61B 1/00154* (2013.01);
(Continued)

(58) Field of Classification Search
CPC ............ A61B 1/00052; A61B 1/00066; A61B 1/00135; A61B 1/00154; A61B 1/015; A61B 1/018; A61B 1/3135
See application file for complete search history.

(56) References Cited

U.S. PATENT DOCUMENTS 2,112,056 A    3/1938   Wappler
3,763,843 A  * 10/1973  Fisher ................... F41B 11/723
                                                    124/69
(Continued)

FOREIGN PATENT DOCUMENTS

CN    101669845    3/2010

OTHER PUBLICATIONS

International Search Report, PCT/US17/34341 dated Oct. 6, 2017; 6pgs.
(Continued)

*Primary Examiner* — Timothy J Neal
(74) *Attorney, Agent, or Firm* — Jennings, Strouss & Salmon PLC; Michael K. Kelly; Daniel R. Pote

(57) ABSTRACT

Methods and apparatus for direct visual rhizotomy using an elongated tubular sheath. The sheath includes: a proximal end configured to removably receive a cannula; a distal end; a horizontal shaft having a longitudinal axis extending between the proximal end and the distal end; a first cut-away generally defining a first plane at the distal end, the first cut-away characterized by a first angle relative to a vertical plane; and a second cut-away generally defining a second plane at the distal end, the second cut-away characterized by a second angle relative to a horizontal plane. The sheath further includes an endoscope camera disposed at the distal end, the camera having a line of sight substantially orthogonal to the first plane.

8 Claims, 20 Drawing Sheets

(51) Int. Cl.
*A61B 1/313* (2006.01)
*A61B 18/14* (2006.01)
*A61B 1/045* (2006.01)
*A61B 17/34* (2006.01)
*A61B 18/00* (2006.01)

(52) U.S. Cl.
CPC .......... *A61B 1/00179* (2013.01); *A61B 1/045* (2013.01); *A61B 1/3135* (2013.01); *A61B 17/3401* (2013.01); *A61B 17/3423* (2013.01); *A61B 17/3468* (2013.01); *A61B 17/3478* (2013.01); *A61B 18/148* (2013.01); *A61B 2017/3437* (2013.01); *A61B 2017/3447* (2013.01); *A61B 2018/0044* (2013.01); *A61B 2018/00339* (2013.01); *A61B 2018/00434* (2013.01); *A61B 2018/00589* (2013.01); *A61B 2018/00595* (2013.01); *A61B 2018/00601* (2013.01); *A61B 2218/002* (2013.01)

(56) References Cited

U.S. PATENT DOCUMENTS

| | | | |
|---|---|---|---|
| 4,239,296 A * | 12/1980 | Kaub | B60T 8/282 303/9.68 |
| 4,335,713 A * | 6/1982 | Komiya | A61B 1/227 600/114 |
| 4,345,589 A * | 8/1982 | Hiltebrandt | A61B 1/00105 348/E5.047 |
| 4,503,843 A * | 3/1985 | Boebel | A61B 1/303 600/114 |
| 4,576,147 A | 3/1986 | Hashiguchi | |
| 4,624,243 A * | 11/1986 | Lowery | A61B 1/00165 600/114 |
| 4,697,577 A | 10/1987 | Forkner | |
| 4,850,342 A | 7/1989 | Hashiguchi et al. | |
| 5,169,397 A * | 12/1992 | Sakashita | A61B 1/00071 600/105 |
| 5,554,100 A | 9/1996 | Leiner et al. | |
| 5,569,183 A | 10/1996 | Kieturakis | |
| 6,007,483 A | 12/1999 | Kieturakis | |
| 6,032,673 A * | 3/2000 | Savage | A61B 18/1485 128/898 |
| 6,494,881 B1 * | 12/2002 | Bales | A61B 18/149 606/41 |
| 6,916,286 B2 | 7/2005 | Kazakevich | |
| 8,208,995 B2 | 6/2012 | Tearney et al. | |
| 8,391,571 B2 | 3/2013 | Cinquin et al. | |
| 8,409,080 B2 | 4/2013 | Gumbs et al. | |
| 9,687,142 B1 | 6/2017 | Lieberman et al. | |
| 2007/0129719 A1 | 6/2007 | Kendale | |
| 2009/0187072 A1 | 7/2009 | Manohara | |
| 2009/0292361 A1 | 11/2009 | Lopez | |
| 2010/0069912 A1 | 3/2010 | McCormack et al. | |
| 2012/0016192 A1 | 1/2012 | Jansen et al. | |
| 2012/0059470 A1 | 3/2012 | Weiman | |
| 2012/0071714 A1 | 3/2012 | Jansen | |
| 2012/0095458 A1 * | 4/2012 | Cybulski | A61B 1/00071 606/41 |
| 2012/0123206 A1 | 5/2012 | Vargas | |
| 2014/0194683 A1 | 7/2014 | Nagaguchi | |
| 2014/0276015 A1 | 9/2014 | Whiseant | |
| 2015/0196193 A1 * | 7/2015 | Kienzle | A61B 1/00066 600/109 |
| 2015/0257629 A1 | 9/2015 | Shanninain | |
| 2015/0289755 A1 | 10/2015 | Voros et al. | |
| 2016/0106551 A1 | 4/2016 | Grimberg et al. | |

OTHER PUBLICATIONS

Written Opinion, PCT/US17/34341 dated Oct. 6, 2017; 6pgs.
International Search Report, PCT/US17/62091 dated Feb. 5, 2018; 3pgs.
Written Opinion, PCT/US17/62091 dated Feb. 5, 2018; 8pgs.

* cited by examiner

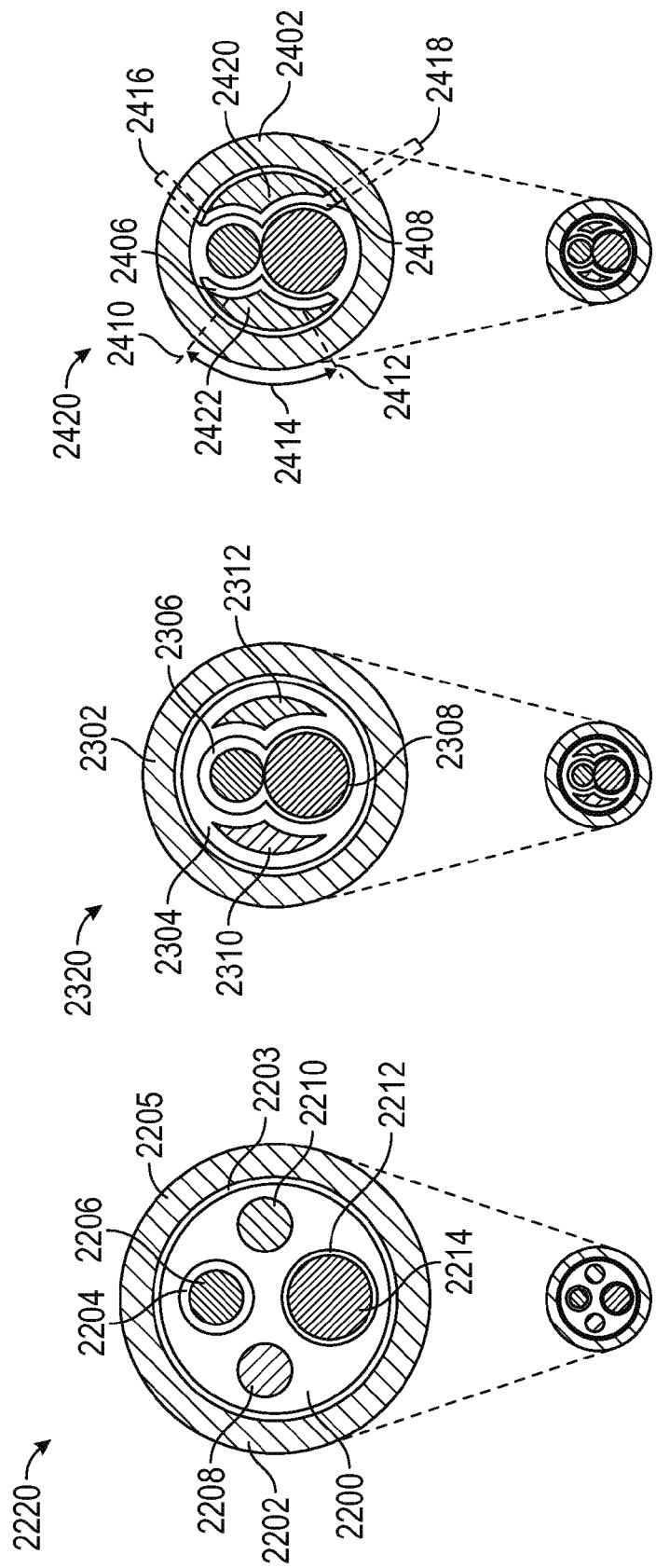

METHODS AND APPARATUS FOR FACILITATING DIRECT VISUALIZED RHIZOTOMY

TECHNICAL FIELD

The present invention relates, generally, to methods and apparatus for facilitating direct visualized rhizotomy (DVR) procedures and, more particularly, to a low profile DVR sheath configured for secure placement on the transverse process.

BACKGROUND

Other than the common cold, back pain is the number one reason people visit a doctor in the United States. There are three principle sources of back pain: i) joint pain (40%); ii) pain from a nerve root (40%); and iii) disc pain (20%). Mature and robust treatment regimens have been developed for disc and root pain including surgical, non-surgical, and epidural modalities. Effective treatment for joint pain has only emerged within the last decade, and to the present day remains elusive with only moderate success.

Spinal joint pain occurs in the facet joint between adjacent vertebrae. The five facet joints on each side of the lumbar spine produce pain signals when they become arthritic or because of injury due to trauma, with 90% of cases occurring at the L4/L5 and L5/S1 junctions. The spinal nerve root, which runs through the spinal column, innervates the vertebrae with two small medial nerve branches, called twigs. Each twig extends across a transverse process associated with each vertebral body. Nerves can have three types of fibers: motor, sensory, and autonomic. The twigs at issue are only sensory; that is, their sole function is to transmit pain via pressure, chemical, and pure pain receptors.

Consequently, cutting a medial branch of the spinal nerve root (the twig) permanently prevents it from transmitting pain signals from the joint to the brain, without compromising any motor or autonomic functionality; that is, cutting the twig stops the pain with no corresponding degradation in nerve function. Pain doctors in the medical community initially began burning the twigs with radio frequency ablation therapies, using the tip of a needle to electrocute the twig. However, radio frequency ablation therapies do not give the surgeon a very good view of the twig and, as such, the pain returned in a significant percentage of patients as twigs often grew back due to incomplete ablation.

The limited success of radio frequency ablation gave rise to the development of endoscopic attempts to more completely sever the twig, using an endoscope to bring a small camera and a light source to give the surgeon a better view of the twig during surgery. This allows the surgeon to physically cut the twig, rather than burn it through ablation, to ensure that the twig is completely severed and reduce the likelihood that the pain will subsequently return.

Presently known endoscopic techniques involve inserting a dilator into the patient, where the dilator has a radiolucent strip to allow the surgeon to locate the tip of the dilator proximate the twig under X-ray. A sheath is inserted over the dilator, and the dilator is withdrawn from the patient. An endoscope is then inserted into the sheath. Prior art endoscope cannula assemblies include 3 distinct channels: i) irrigation supply and return; ii) endoscopic probe having a camera and a slot for receiving a coagulator; and iii) a light source. Presently known endoscopic tools used for coagulating twigs at the transverse process were adapted from analogous tools developed for disc surgery, and are not well suited for use in the context of the present invention. For example, presently know endoscopic sheaths have a larger diameter than necessary to perform the function of severing the twig, and the distal tip of the sheath—having been developed for disc surgery—is not well adapted for stable placement on the transverse process.

Methods and apparatus are thus needed which overcome these and other limitations of the prior art.

Various features and characteristics will also become apparent from the subsequent detailed description and the appended claims, taken in conjunction with the accompanying drawings and this background section.

BRIEF SUMMARY

Various embodiments of the present invention relate to methods and apparatus for, inter alia: i) providing a sheath with a distal end configured to rest on the transverse process proximate the medial nerve root branch (twig) in a stable manner; ii) providing a resiliently deformable spring mechanism for moving the endoscope camera back and forth along the sheath axis proximate the twig in a controlled manner; iii) reducing the overall cross sectional area of the endoscope assembly by employing optimally shaped fluid ingress and egress channels; iv) providing a novel cannula configuration which facilitates fluid ingress and egress without the need for supplemental suction; v) providing a sheath aperture which is substantially parallel to the plane of the camera (substantially orthogonal to the camera line of sight) to thereby optimize the endoscopic field of view; and vi) providing a stable platform for allowing the surgeon to cut through the twig orthogonally by simply extending and retracting the electrode, either manually or automatically via a resiliently deformable (e.g., elastomeric) spring.

It should be noted that the various inventions described herein, while illustrated in the context of a direct visualized rhizotomy (DVR) procedure, are not so limited. Those skilled in the art will appreciate that the inventions described herein may contemplate any procedure in which it is desired to transiently dock or otherwise stabilize an endoscopic device on an anatomical surface.

Various other embodiments, aspects, and features are described in greater detail below.

BRIEF DESCRIPTION OF THE DRAWING FIGURES

Exemplary embodiments will hereinafter be described in conjunction with the following drawing figures, wherein like numerals denote like elements, and:

FIG. 22 is schematic cross-section view of a DVR assembly including a cannula configuration defining respective endoscope, electrode, fluid ingress, and fluid egress wholly contained within the cannula structure in accordance with various embodiments;

FIG. 23 is schematic cross-section view generally to FIG. 22, in which the endoscope and electrode channels partially intersect, and further wherein the fluid ingress and egress channels are noncircular yet wholly contained within the cannula structure in accordance with various embodiments;

FIG. 24 is schematic cross-section view of a DVR assembly generally analogous to FIGS. 22 and 23, in which the endoscope and electrode channels partially intersect, and further wherein the fluid ingress and egress channels are partially bounded by the inner wall of the sheath in accordance with various embodiments;

Figure 25:
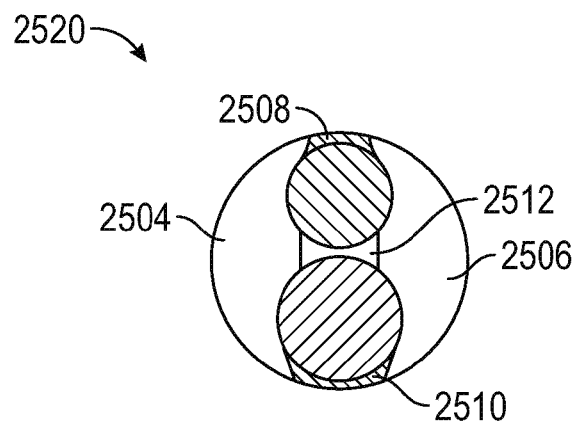
Figure 26:
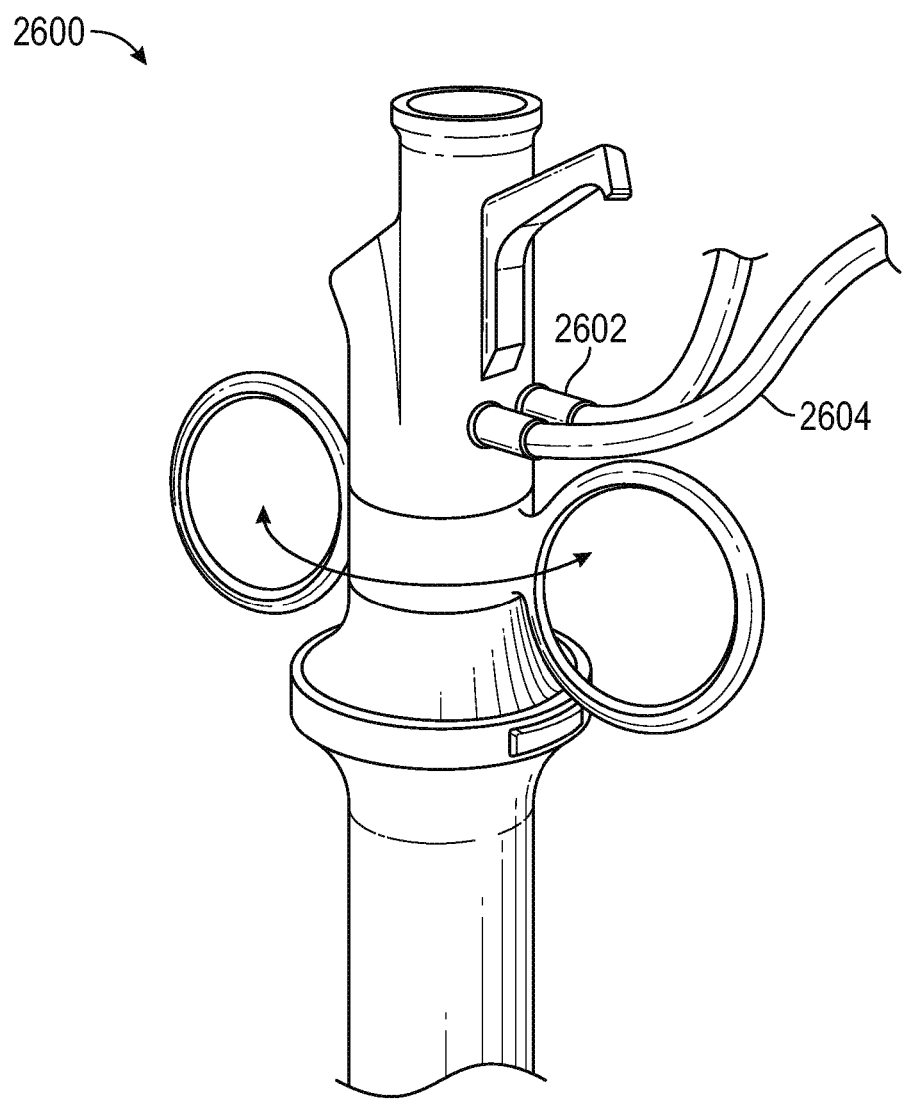
Figure 27:
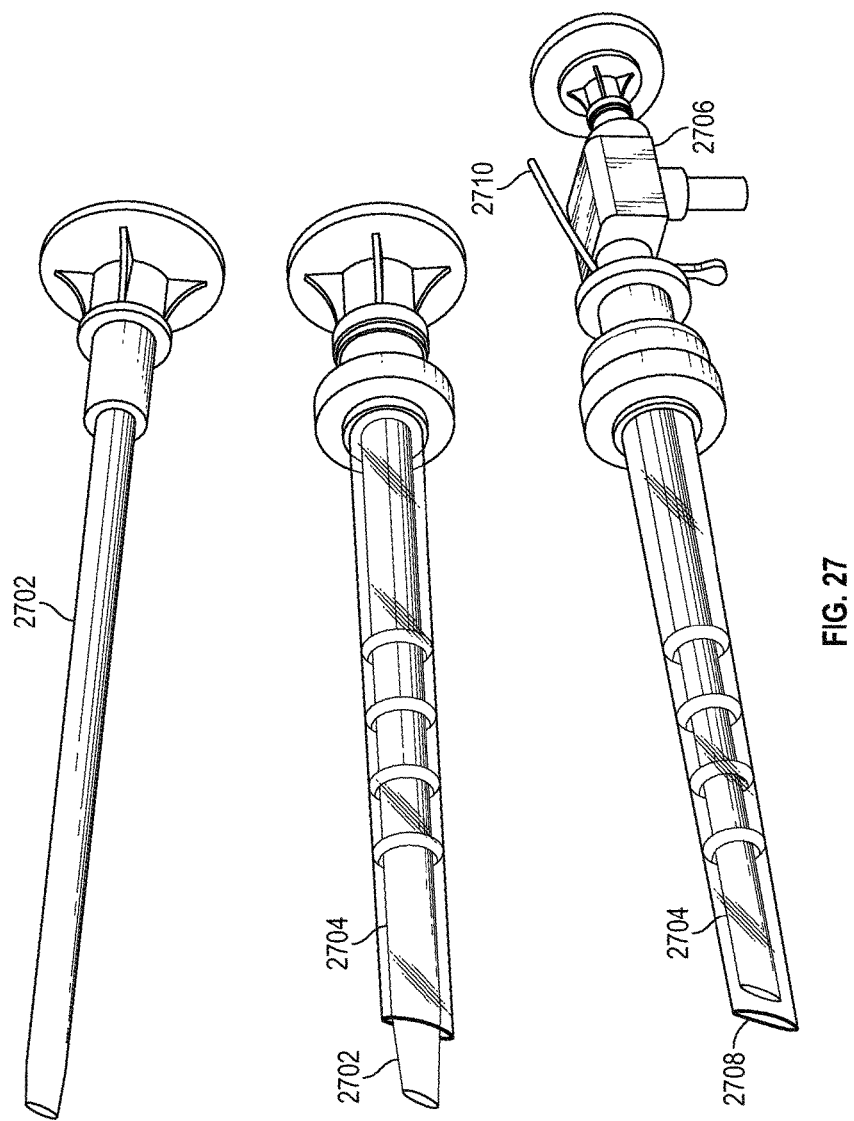
Figure 28:
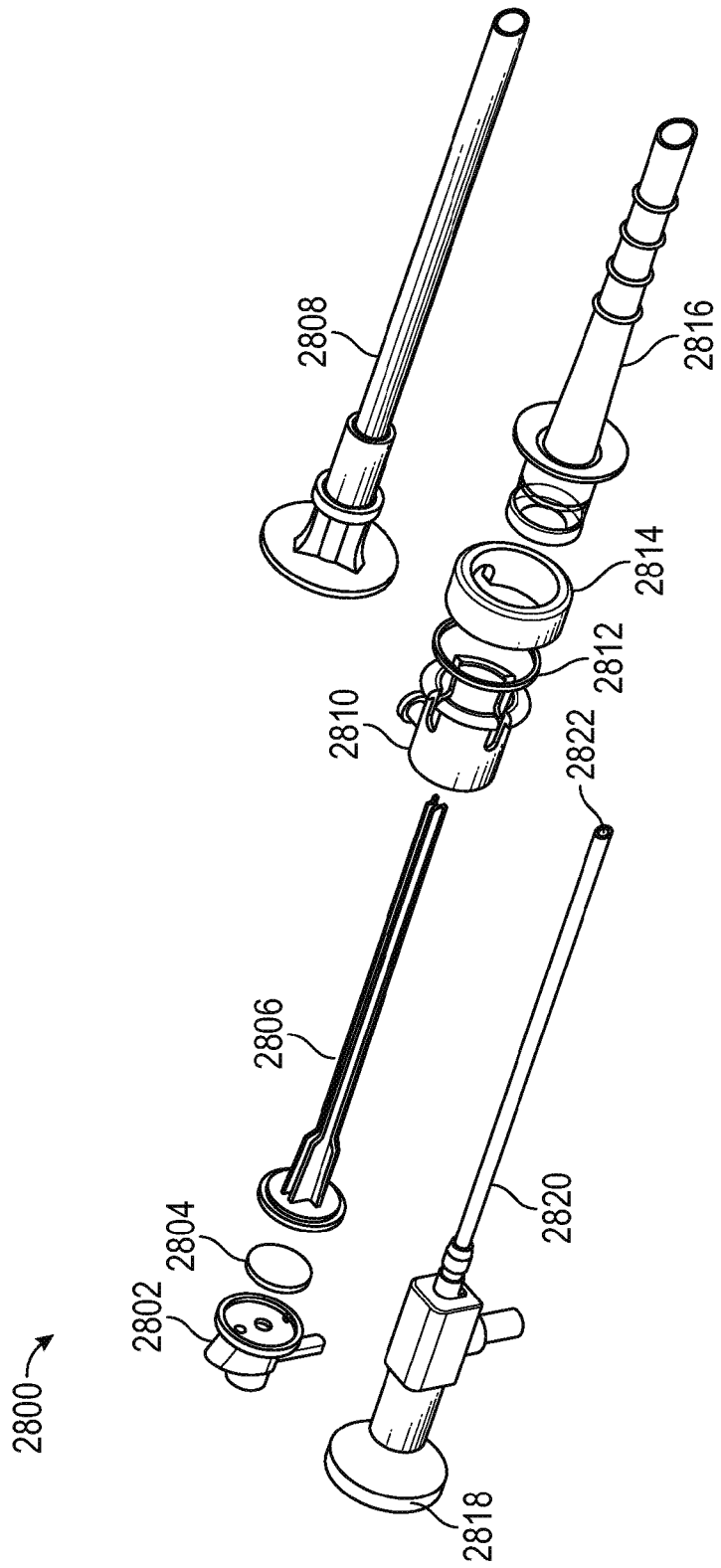
Figure 29:
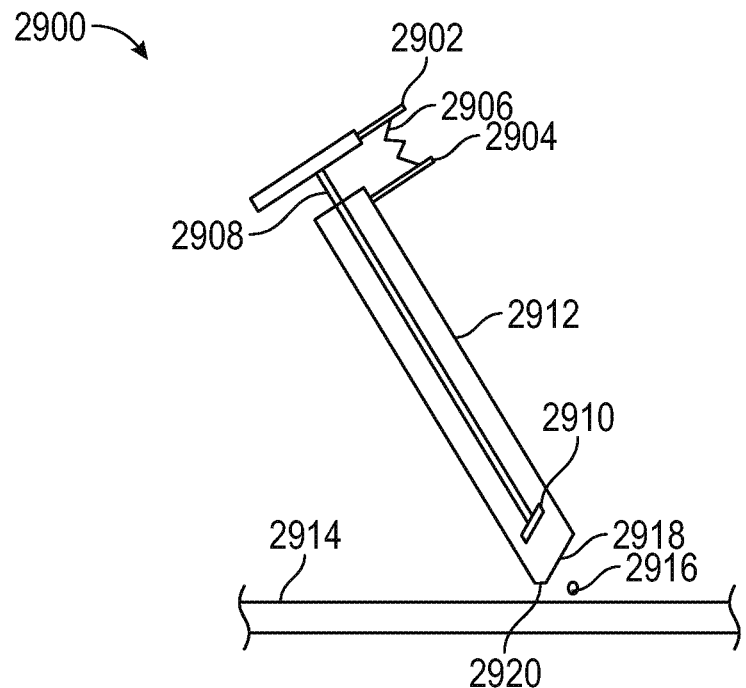
Figure 30:
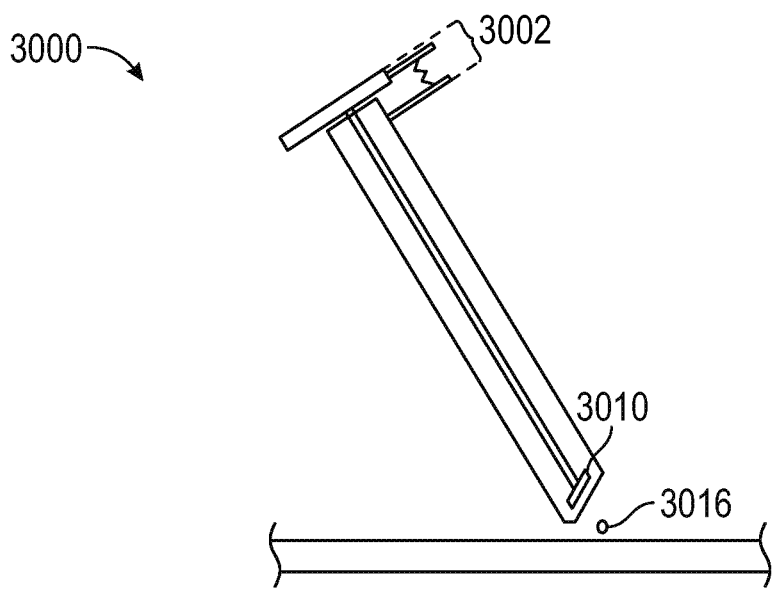
Figure 31:
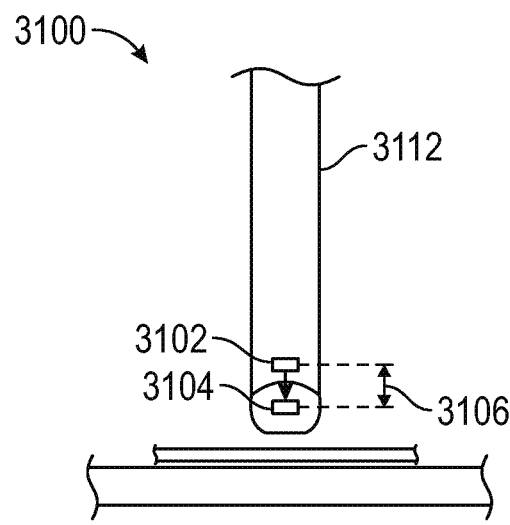
Figure 32:
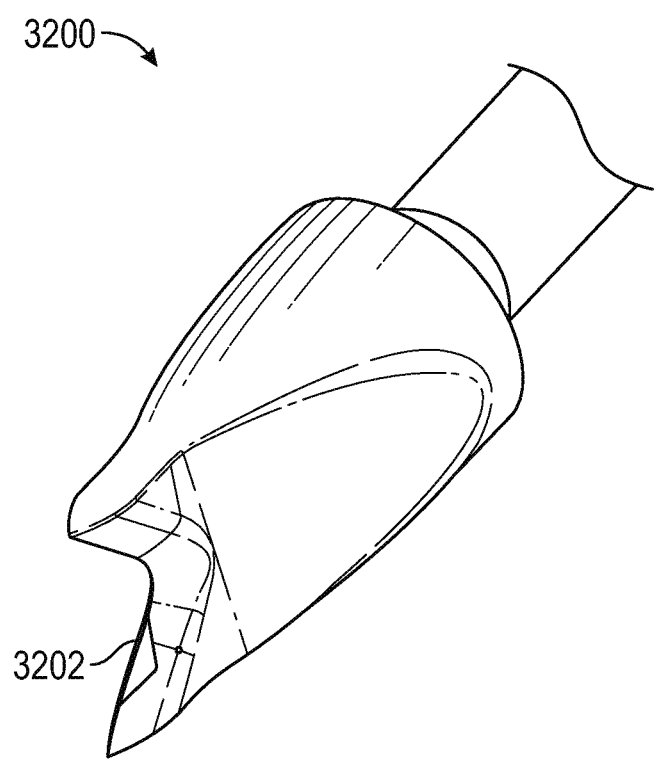
Figure 33:
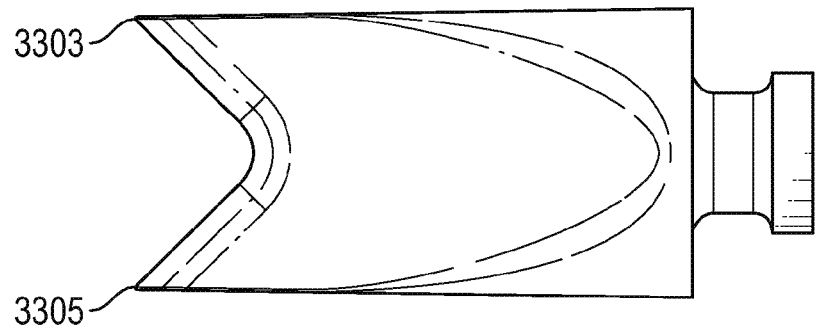
Figure 34:
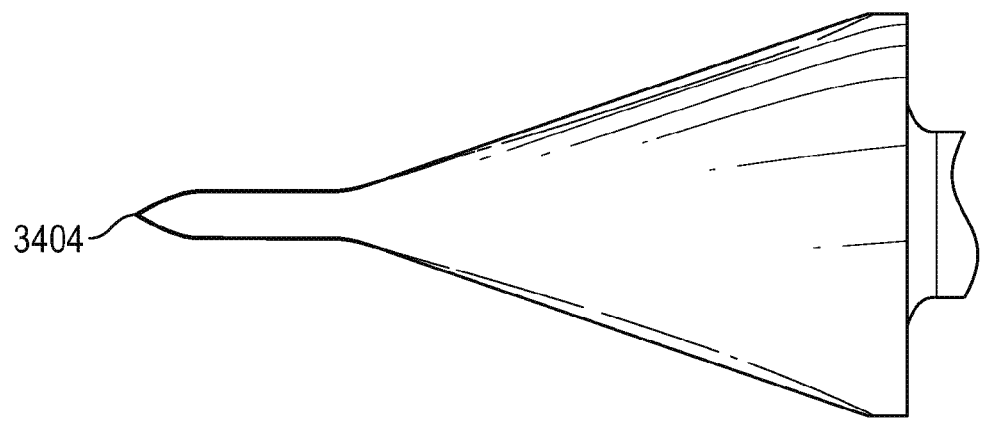

FIG. 25 is schematic cross-section view of a DVR assembly generally analogous to FIGS. 22-24, in which the endoscope and electrode are guided by minimal cannula structure extending radially inwardly from the inner wall of the sheath, and further wherein the fluid ingress and egress channels have an inside boundary defined by one or both of the electrode and endoscope, and an outside boundary defined by the sheath wall in accordance with various embodiments;

FIG. 26 is a perspective view of a DVR device showing external fluid ingress and egress connections for use both with and without supplemental suction in accordance with various embodiments;

FIG. 27 is perspective view of a dilator, a dilator in the sheath, and a cannula including an endoscope and electrode in the sheath in accordance with various embodiments;

FIG. 28 is a perspective exploded view of the components shown in FIG. 27 in accordance with various embodiments;

FIG. 29 is a schematic view of an endoscope in the sheath depicting the camera in a retracted position in accordance with various embodiments;

FIG. 30 is a schematic view of the endoscope in the sheath shown in FIG. 29, depicting the camera in an extended position as a result of compressing the elastomeric spring in accordance with various embodiments;

FIG. 31 is a schematic view illustrating the retracted and extended positions of the camera shown in FIGS. 29 and 30 in accordance with various embodiments;

FIG. 32 is a perspective view of a dilator having a chisel configured to scrape the transverse process or other anatomical surface to provide a secure footing in accordance with various embodiments;

FIG. 33 is a top view of the dilator shown in FIG. 32 in accordance with various embodiments; and FIG. 34 is a side view of the dilator shown in FIG. 32 in accordance with various embodiments.

DETAILED DESCRIPTION OF PREFERRED EXEMPLARY EMBODIMENTS

The following detailed description of the invention is merely exemplary in nature and is not intended to limit the invention or the application and uses of the invention. Furthermore, there is no intention to be bound by any theory presented in the preceding background or the following detailed description.

Various embodiments of the present invention relate devices and associated methods for performing endoscopic procedure, such as direct visualized rhizotomy in which a small, hair-like nerve branch is coagulated or otherwise severed to prevent it from transmitting pain signals from a facet joint.

By way of brief introduction, each vertebral body (e.g., lumbar vertebrates L4, L5) in the human spine has an upper extending process and a lower extending process; adjacent upper and lower extending processes together form a facet joint. Every facet joint is innervated by two hair-like medial nerve branches (referred to herein as twigs), and every medial branch innervates two joints. In addition, each vertebral body further includes respective left and right transverse processes, across which the twig extends. Although the surface of the transverse process is modeled as a substantially flat, horizontal surface to facilitate this discussion, those skilled in the art will appreciate that an actual transverse surface is irregular, and generally convex.

When the facet joint becomes inflamed, the twig transmits pain signals to the brain. Rather than attempt to address the source of inflammation, it is sometimes easier to simply sever the twig. Indeed, for some patients this is the only therapeutic intervention that can provide relief from what is often debilitating, chronic pain.

In an embodiment, a dilator tool is inserted into a sheath, and the dilator/sheath assembly is used to cut thru the patient's skin and underlying tissue until the terminal end of the assembly is positioned proximate the transverse process. The surgeon then removes the dilator, leaving the sheath in place. Inserting a cannula (including an endoscope) into the sheath provides the surgeon with a live visual of the medial branch and surrounding tissue displayed on a screen or monitor. The endoscope uses a pressurized saline solution (water) to dilate the surrounding tissue and create a "bubble" which functions as working space at the twig site.

With the sheath resting on the transverse process proximate the twig, a coagulating electrode may be inserted through the cannula and extended to the twig location, whereupon the electrode is actuated to cut across the twig, using the electrode as a dissector. In various embodiments, the sheath and cannula of the present invention may be configured to accommodate any number of the various industry standard and widely available endoscopes, such as those available from Stryker™ of Kalamazoo, Mich., Medtronic™ of Minneapolis, Minn., and Karl Storz of Germany.

The boney transverse process (TP) can be seen on the screen using X-ray illumination. To assist the surgeon in placing the distal end of the device on the surface of the transverse process, the dilator and/or sheath may include one or more radiolucent markings. In this way, the surgeon can reliably locate the sheath tip at the twig, knowing that the twig is located on the transverse process. Once the distal end of the dilator/sheath assembly is maneuvered into position on the transverse process, the dilator is removed from the sheath and replaced with the cannulated endoscope, which may be secured in the sheath using a collet lock or any other desired mechanism. The endoscope may then be used to definitively orient the cauterizer (electrode) at the twig, allowing the surgeon to affirmatively confirm that the cauterizer cuts through the twig while watching the nearby screen in real time.

In an embodiment, the cauterizer or coagulator comprises bipolar active electrode probe available from Ellman™ International of Hicksville, N.Y. In practice, the surgeon pre-sets the voltage (e.g., 40 millivolts), and uses a pedal, switch, verbal command, or other technique to activate the electrode once it is in the proper position proximate the twig. By ensuring that no partial contiguity remains after coagulation, cauterization, or otherwise completely cutting through the twig, the patient can be assured that the nerve cannot recover (grow back). That is, although the proximal and distal ends of the medial branch remain connected to their respective roots, there can be electrical transmission across the twig after it is cut.

Presently known endoscopic tools do not permit transitioning the camera between an retracted position which provides a far field view of the bubble site, and an extended position providing a close up view of the twig, in part because knee and disc surgical procedures focus on objects significantly larger than a twig; hence, there is no need to extend and retract the camera. In accordance with one aspect of the present invention, a neoprene spring allows the surgeon to manually or automatically extend and retract the camera along the cannula axis to controllably transition between a far field and near field view of the sit under inspection. This movement allows the surgeon to obtain an up close view of the region to be cut, then retract the camera to obtain a broader perspective during the actual cutting; alternatively, the surgeon may view the surrounding tissue at a distance, then bring the camera in close to the twig during actual cutting.

In an embodiment, the endoscope assembly may include opposing surfaces, handles, loops, or the like for the thumb and a finger (e.g., forefinger) to squeeze a trigger formed by the opposing surfaces to thereby move the camera from the retracted position to the extended position; when thumb/finger pressure is gradually released, the resilient spring returns the camera to the retracted position. The spring mechanism may be configured to avoid jerky visual artifacts.

In another embodiment, an analogous trigger mechanism may be employed to controllably move the electrode tip through the twig during cutting.

In accordance with a further aspect of the invention, the distal end of the sheath may be configured to provide an aperture having a size, shape, orientation, and configuration optimized for cutting a twig on the surface of the transverse process. For example, if the aperture is too large or at too step an angle relative to the sheath axis, adjacent soft tissue may obscure the field of view. In an embodiment, a flat or concave cut-away is made in the distal end of the sheath to create an aperture which looks upwardly, for example in the range of 30° from the sheath axis. Those skilled in the art will appreciate that this allows the aperture to remain generally parallel to the plane of the endoscope camera, which typically tilts upward at a 30° angle from the sheath axis.

In a preferred embodiment, a secondary cut-away is then formed in the bottom of the sheath, creating a flat or concave surface to rest on the convex surface of the transverse process during cutting of the twig (whereas a rounded tip tends to roll on the TP surface). Placing a cut-out (or "flat") on the distal end of the angled sheath tip allows the sheath to firmly rest on the transverse process. The secondary cut-out can be flat, concave, or any desired geometry to facilitate transient docking of the device on the TP.

The present inventor has further determined that presently known cannula designs do not adequately balance the need for a minimally invasive device profile (cross section) with the need to irrigate the surgical site to create the working pressure bubble. In particular, using circular channels for fluid ingress and fluid egress along the cannula results in unnecessary cannula structure, which takes up space within the sheath which could otherwise be used for irrigation. Accordingly, in an embodiment, non-circular fluid ingress and/or egress channels are employed to reduce the overall cross sectional profile of the device, while still allowing sufficient fluid flow.

More particularly, the cross-sectional shape of one or both of the fluid ingress and egress channels may include two components: i) an arc segment of outer diameter of one or both of the coagulator and endoscope channels if these channels are circular in cross-section; otherwise this first component may comprise a segment of the outer perimeter of one or both of the coagulator and endoscope channels; and ii) an arc segment of the sheath inner diameter if the sheath has a circular cross-section; otherwise this second component may comprise a segment of the inner perimeter of the sheath.

By configuring the cross-sectional shape of the ingress and egress channels to utilize "what's left" after subtracting the (typically) circular cross sectional areas for the coagulator and endoscope channels, endoscope assembly may occupy a smaller total cross sectional area as compared with ingress and egress channels having circular cross sections.

Referring now to FIGS. 1-8, various aspects of the present invention will now be described in conjunction with an exemplary direct visual rhizotomy (DVR) surgical procedure.

Figure 1:
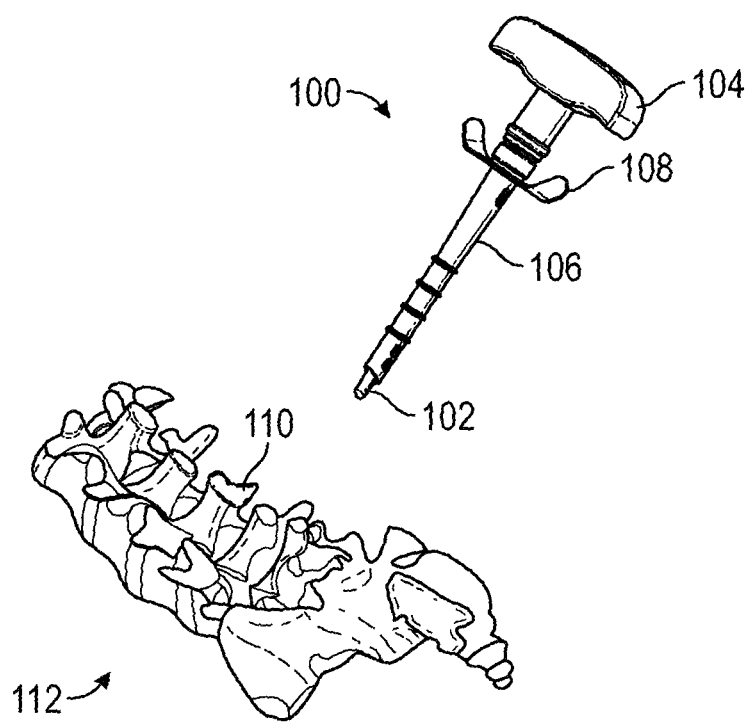
FIG. 1 is a perspective view of a dilator and sheath assembly as introduced for use in a direct visual rhizotomy (DVR) surgical procedure in accordance with various embodiments.

More particularly, FIG. 1 is a perspective view of a dilator and sheath assembly 100 as these components may introduced for use in a DVR procedure on a vertebral body 110 of a human or animal spine 112. Specifically, the dilator/sheath assembly 100 includes a dilator tool having a distal tip 102 and a handle 104 slidably disposed within a sheath 106. The sheath 106 may include grips 108 to facilitate the insertion, removal, and manipulation of the dilator, cannula, and endoscope, and electrode, as described in greater detail below.

Figure 2:
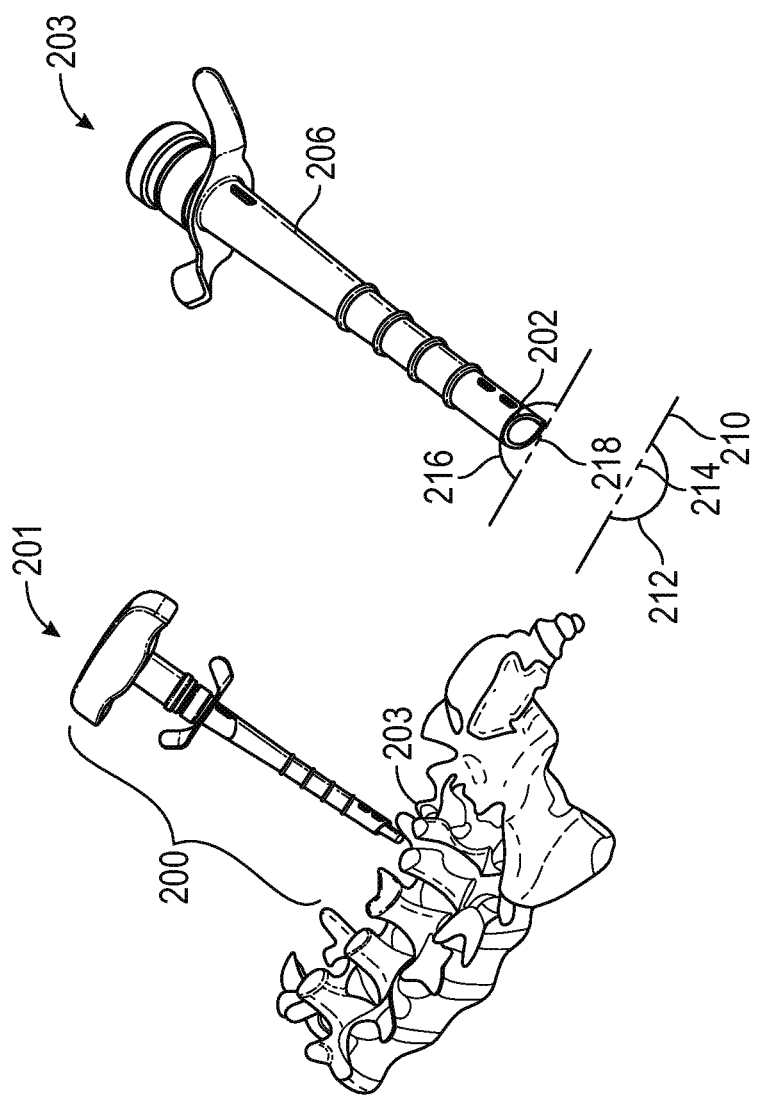
FIG. 2 is a perspective view of the dilator and sheath assembly as inserted into the patient in a DVR procedure, illustrating the placement of the distal end of the sheath on a transverse process proximate a medial branch of the spinal nerve root in accordance with various embodiments.

FIG. 2 includes a first view 201 and a second view 203. The first view 201 shows a dilator sheath assembly 200 inserted into the patient such that the tip of the dilator/sheath assembly is adjacent a transverse process 203. As briefly discussed above, once the tip is in place proximate the transverse process, the surgeon removes the dilator to allow the cannula to be inserted into the sheath. The second view 203 shows the sheath 206 with the dilator removed and before the cannula is inserted into the sheath. As shown in view 203, the vertebral body 210 includes a left transverse process 212 having a twig 214 extending thereacross, and a right transverse process 216 having a twig 218 extending thereacross. Note that the tip 202 of the sheath suitably rests on the transverse process 216 proximate the twig 218. As described in greater detail below, the tip 202 of the sheath incorporates a first (upper) cut-away configured to provide an optimum field of view for the endoscope camera, and a second (lower) cut-away configured to allow the sheath to rest on the transverse process in a stable manner during the cutting portion of the DVR procedure.

Figure 3:
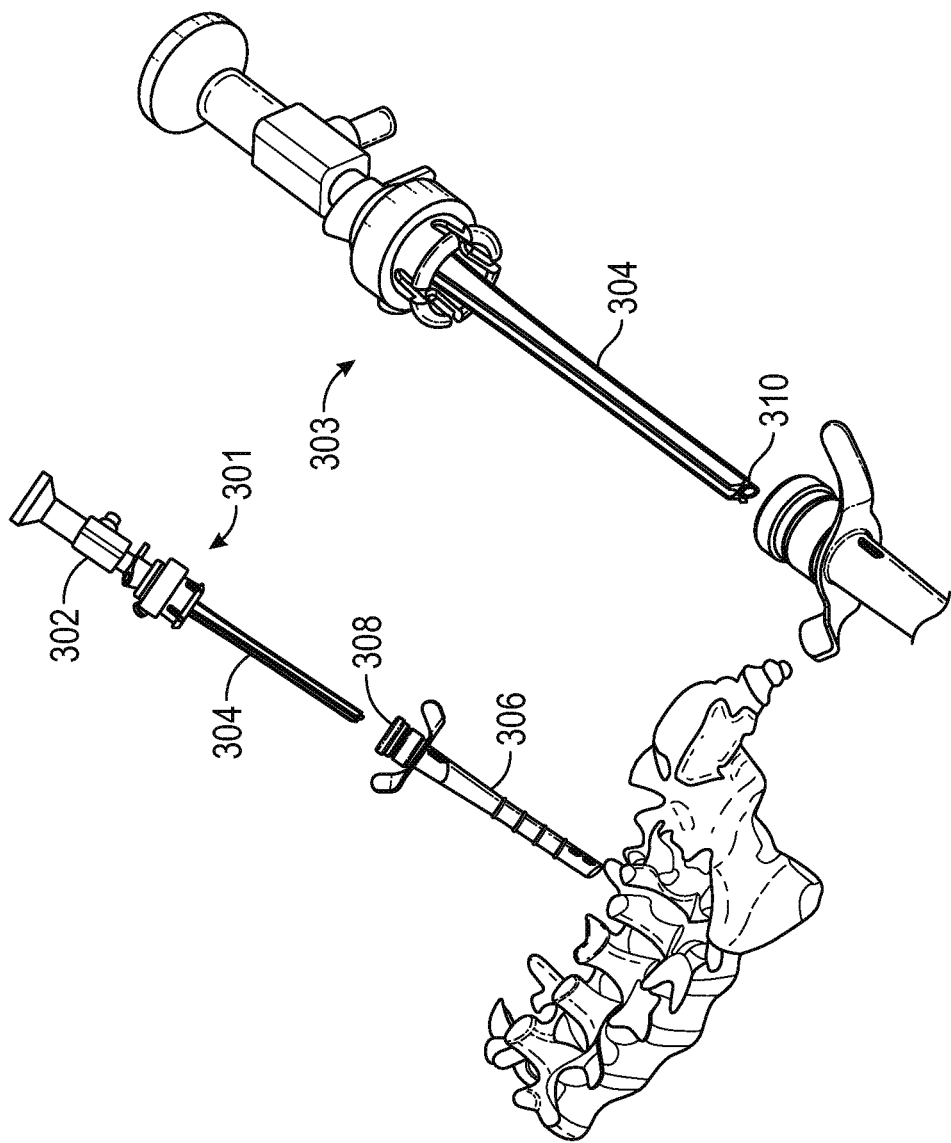
FIG. 3 is a perspective view of a cannula and sheath assembly as introduced for use in a DVR procedure, illustrating a ribbed cannula configuration in accordance with various embodiments.

FIG. 3 shows a first view 301 of a cannula having a ribbed shaft 304 with an attached endoscope 302 being inserted into a sheath 306 previously positioned on the transverse process as described above. FIG. 3 also includes a second view 303 showing a close up of an endoscope camera 310 at the distal end of an endoscope channel, described in greater detail below.

Figure 4:
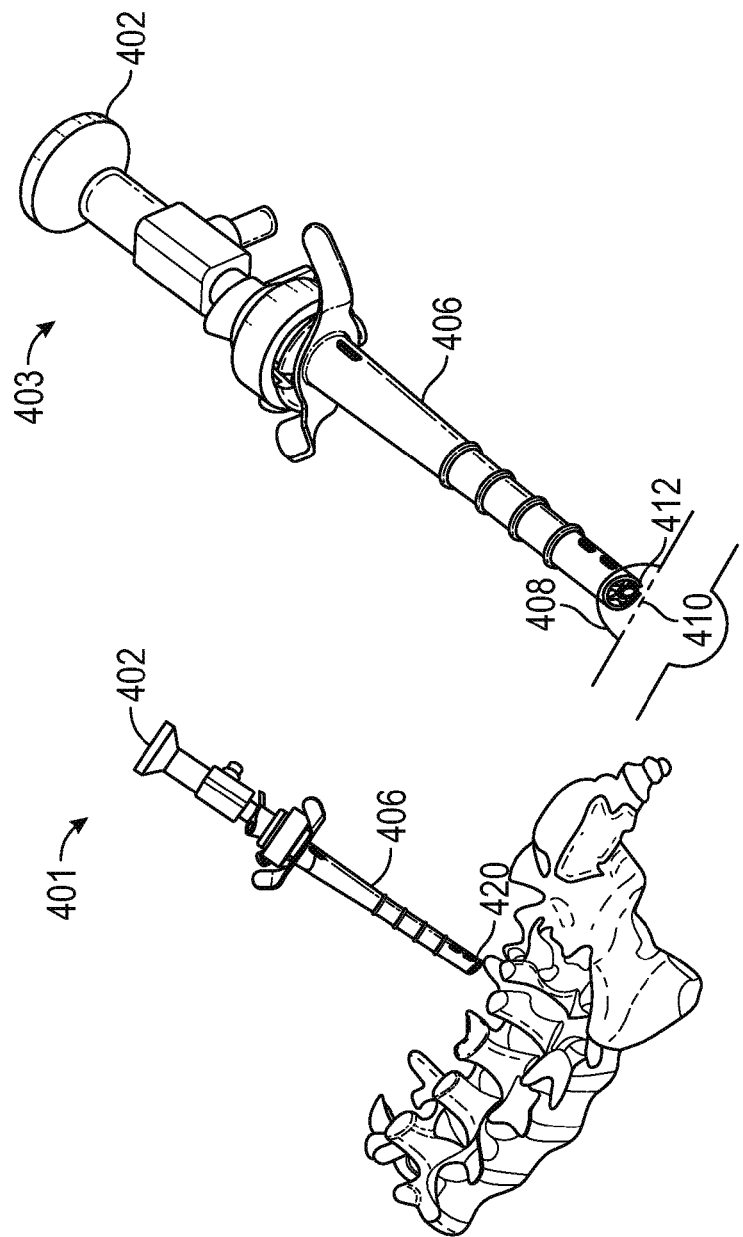
FIG. 4 is a perspective view of the cannula and sheath assembly as inserted into the patient in a DVR procedure, illustrating the placement of the distal end of the cannula and sheath assembly on the transverse process proximate a medial branch of the spinal nerve root in accordance with various embodiments.

FIG. 4 includes a first view 401 showing an endoscope 402 received within an endoscope channel in the cannula shaft (not shown in FIG. 4), with the endoscope and cannula inserted into a sheath 406 such that the distal tip 420 of the cannula assembly rests on the transverse process. A second view 403 depicts a second cut-away 412 in the sheath tip configured to rest on a transverse process surface 408 proximate a medial branch (twig) 410. In an embodiment, the shape (e.g., radius) of the concavity of cut-away 412 suitably generally corresponds to the convexity of the transverse process surface.

Figure 6:
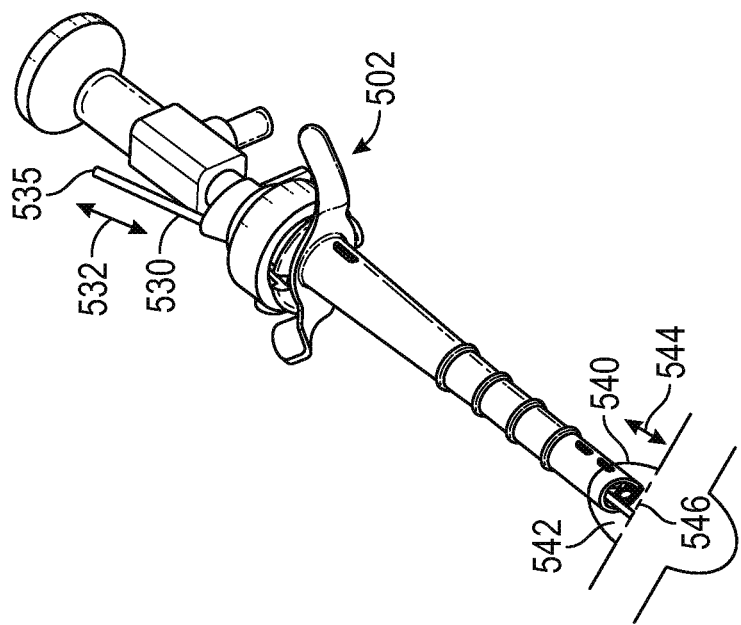
FIG. 6 is a perspective view of the cannula and sheath assembly of FIG. 5, illustrating the manual and/or automatic axial extension of the probe to cut across and thereby coagulate the medial branch in accordance with various embodiments.
Figure 5:
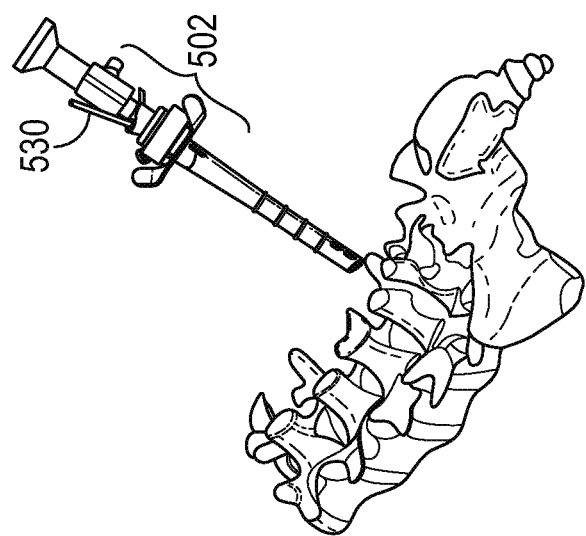
FIG. 5 is a perspective view of the cannula and sheath assembly of FIG. 4, with a bipolar probe inserted through the cannula, in accordance with various embodiments.

Once the surgeon confirms that the tip of the sheath is proximate the twig, for example by viewing a live feed video monitor displaying the output signal from the endoscope camera, a bi-polar probe or other tool for cutting, coagulating, cauterizing, burning, slicing, cutting, or otherwise severing the twig may be inserted through the cannula to the twig site. More particularly, FIG. 5 depicts an electrode 530 being inserted into a cannula assembly 501. FIG. 6 depicts movement 532 (either manual or automatic) of a proximal end 535 of the electrode 530 along the axis of the endoscope. This movement along arrow 535 results in corresponding movement of a distal end 542 of the electrode 530 along arrows 544 to thereby cut through the twig 546 and complete the DVR procedure.

Figure 7:
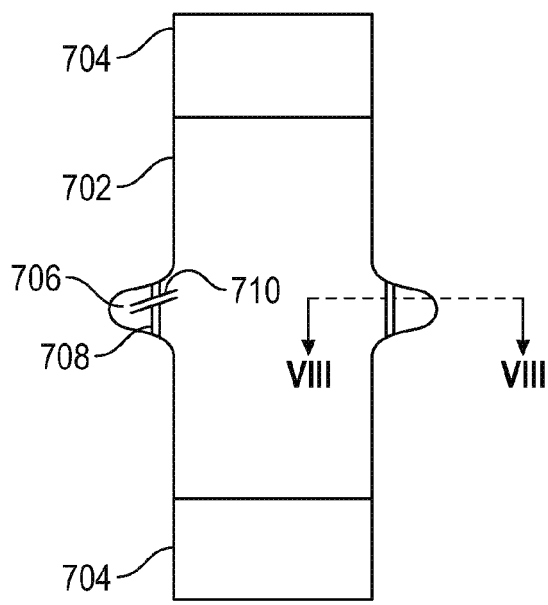
FIG. 7 is a schematic top view of a vertebral body illustrating the position of each medial branch on a corresponding transverse process in accordance with various embodiments.

FIG. 7 is a schematic top view of a vertebral body 702 having respective upper and lower adjacent discs 704 and respective transverse processes 706, each having a medial nerve branch (twig) 708 extending thereacross. The above described DVR procedure culminates in cutting the twig along cut lines 710.

In accordance with various embodiments, the distal end of the sheath includes two cut-aways: i) a first cut-away configured to position the endoscope camera with an optimal field of view of the twig site; and ii) a second cut-away configured to allow the sheath to rest upon the surface of the transverse process immediately proximate the twig.

Figure 8:
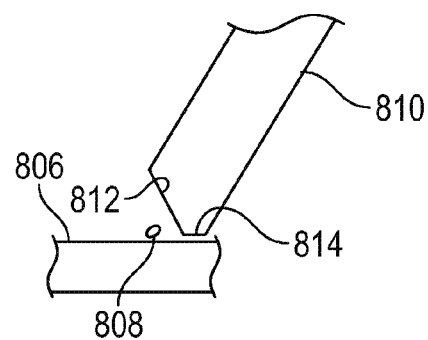
FIG. 8 is a schematic cross-section view taken along line VIII of FIG. 7, illustrating the placement of the sheath on the surface of the transverse process in accordance with various embodiments.

More particularly and referring now to FIG. 8, a schematic cross-section view taken along line VIII of FIG. 7 shows the placement of the sheath on the surface of the transverse process in accordance with various embodiments. In the illustrated embodiment, a sheath 810 comprises a first cut-away 812 configured to afford the endoscope camera (not shown in FIG. 8) an unobstructed line of sight to the twig 808, and a second cut-away 814 configured to rest on the surface 806 of the transverse process.

Figure 9:
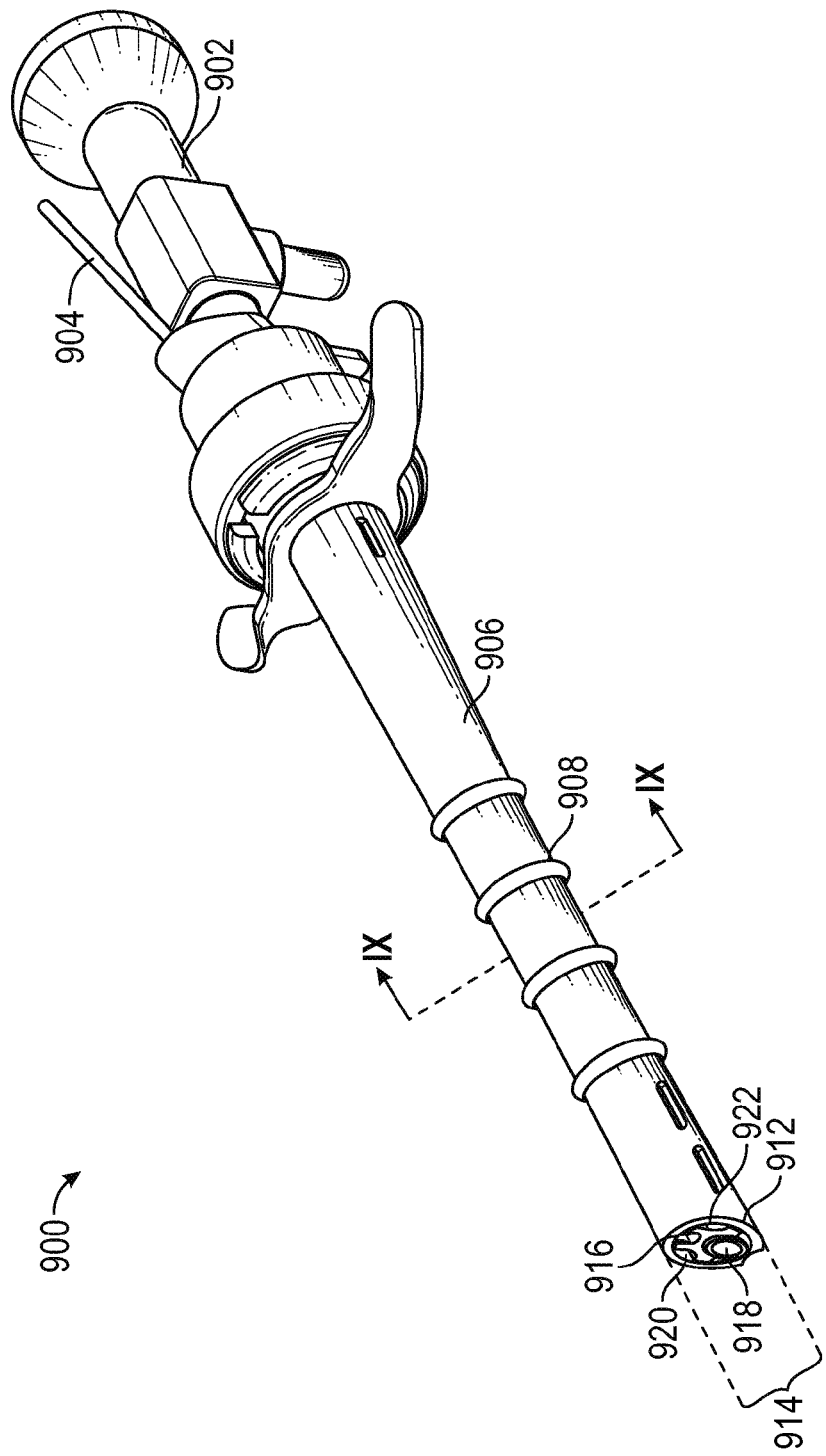
FIG. 9 is a perspective view of an exemplary DVR endoscopic assembly including a sheath, cannula, endoscope, electrode, and fluid ingress and egress channels in accordance with various embodiments.

FIG. 9 is a perspective view of an exemplary DVR endoscopic assembly 900 including an endoscope 902 and an electrode 904 secured within a cannula (not shown inside a sheath 906 having a barbed 908 shaft. The distal end of the sheath (lower left in FIG. 9) includes a first cut-away 912, a second cut-away 914 comprising two prongs configured to allow the sheath to dock on the surface of a transverse process, an endoscope camera 918, a fluid ingress channel 920 and a fluid egress channel 922.

Figure 10:
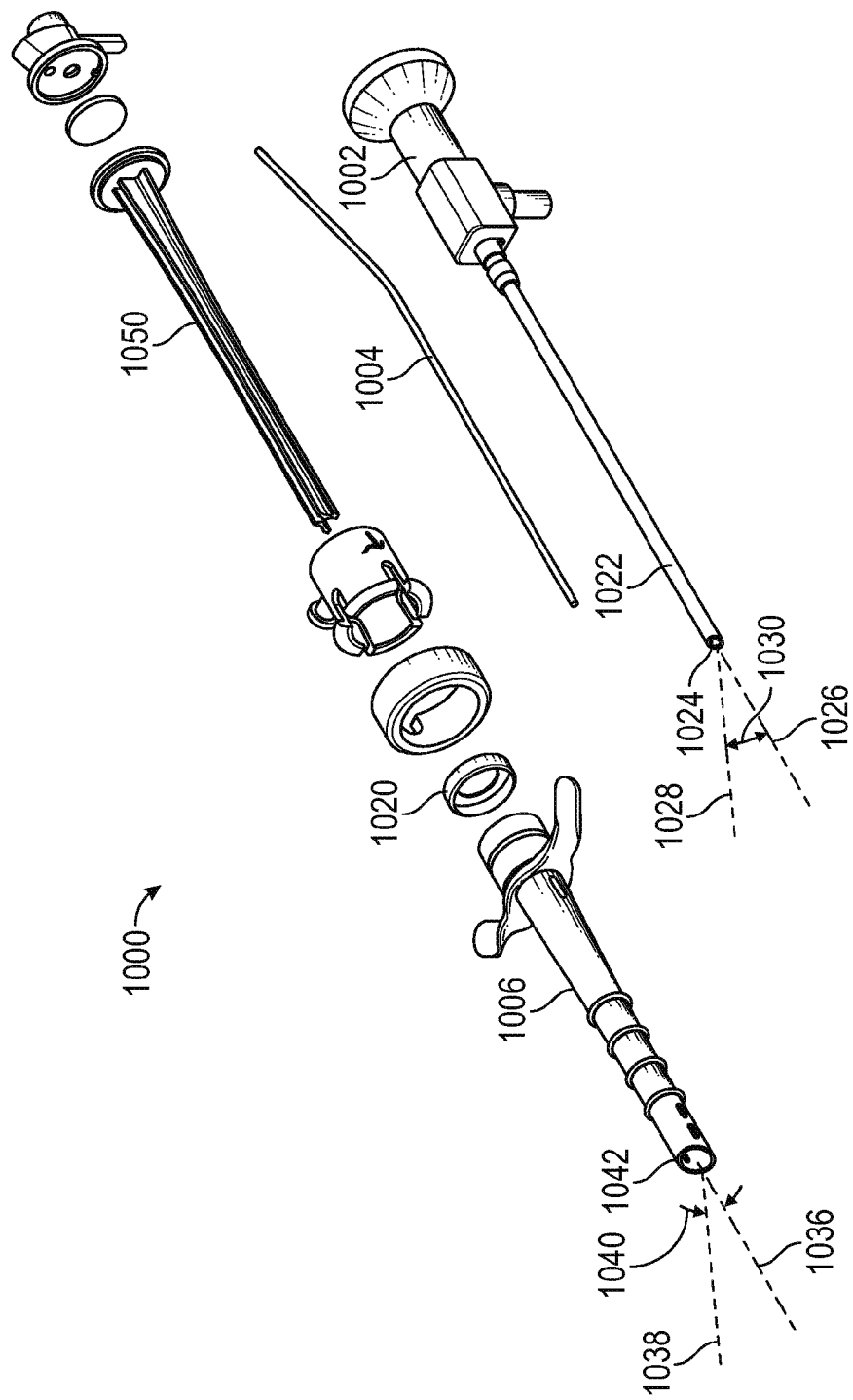
FIG. 10 is an exploded perspective view of the assembly of FIG. 9, illustrating the upward looking angle of the camera line of sight relative to the sheath axis in accordance with various embodiments.

FIG. 10 is an exploded perspective view 1000 of the assembly of FIG. 9, including an endoscope 1002 having a shaft 1022 defining a longitudinal axis 1026, and a camera 1024 having a line of sight along a sight axis 1028 inclined upwardly from the axis 1026 at an angle 1030. In an embodiment, the angle 1030 is in the range of 5 to 75 degrees, and preferably in the range of 20 to 60 degrees, and most preferably about 30 or 45 degrees.

With continued reference to FIG. 10, view moo further includes a ribbed cannula configured to receive endoscope 1002 and an electrode 1004 for receipt within a sheath 1006 having a longitudinal axis 1036, and a resiliently deformable spring 1020 configured to facilitate controlled movement of the camera (and the electrode, if desired) along the sheath axis 1036, as described in greater detail below. The distal end of the sheath 1006 includes a first cut-away 1042 defining an aperture oriented substantially orthogonal to a line of sight 1038. In a preferred embodiment, an angle 1040 defined between the axis 1036 and the line of sight 1038 corresponds to the angle 1030, so that the camera face remains substantially parallel to the plane defined by the first cut-away 1042.

Figure 11:
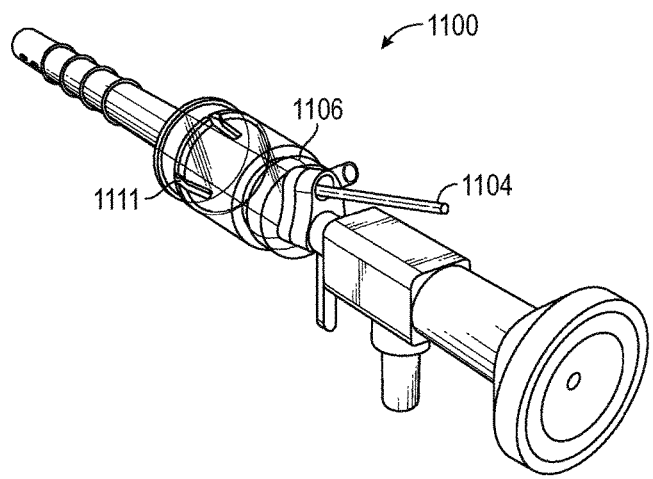
FIG. 11 is a close up view of an exemplary DVR endoscopic assembly, depicting a resiliently deformable spring mechanism for facilitating a controlled transition between axially extended and retracted camera (and/or electrode) positions in accordance with various embodiments.

FIG. 11 is a close up view of an exemplary DVR endoscopic assembly 1100, including a resiliently deformable spring mechanism 1111 for facilitating a controlled transition between axially extended and retracted camera (and/or electrode) positions in accordance with various embodiments. In the illustrated embodiment, an electrode 1104 can be conveniently inserted into and removed from an electrode inlet 1106 to guide the electrode into an electrode channel (not shown in FIG. 11) formed in the cannula, as described in greater detail below.

Figure 12:
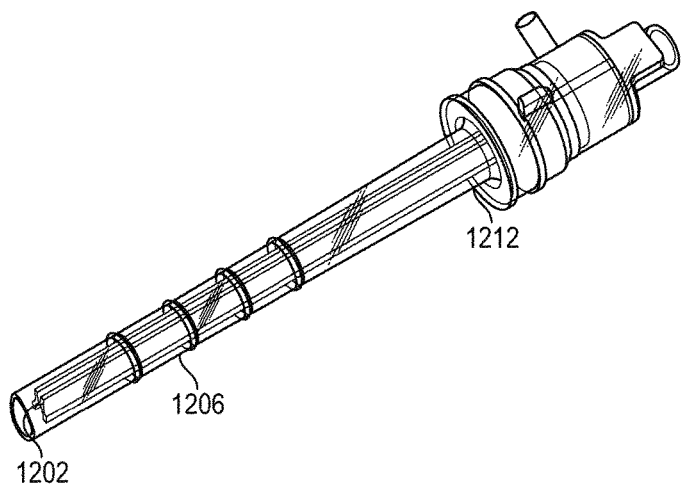
FIG. 12 is a perspective view of the DVR endoscopic assembly of FIGS. 9 and 11 with the endoscope and electrode removed to highlight various details of the cannula, sheath distal end, and the elastomeric component in accordance with various embodiments.

FIG. 12 is a perspective view of an exemplary DVR endoscopic with the endoscope and electrode removed to highlight various details of the cannula 1202 disposed inside the sheath 1206. An exemplary spring 1212 is also shown.

Figure 13:
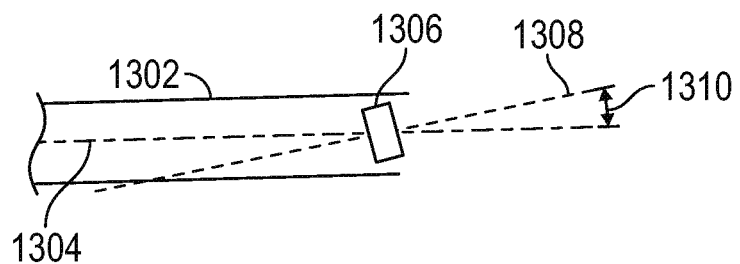
FIG. 13 is a schematic view of a sheath having an aperture orthogonal to the sheath axis in accordance with various embodiments.

FIG. 13 is a schematic view of a sheath having an aperture orthogonal to the sheath axis in accordance with various embodiments. More particularly, a sheath 1302 defines a longitudinal axis 1304. An endoscopic camera 1306 mounted within the sheath is configured to have a line of sight along an axis 1308, defining an angle 1310 with respect to the axis 1304. The value of the angle 1310 is generally analogous to the angle 1030 discussed above in conjunction with FIG. 10, namely about 30°.

Figure 14:
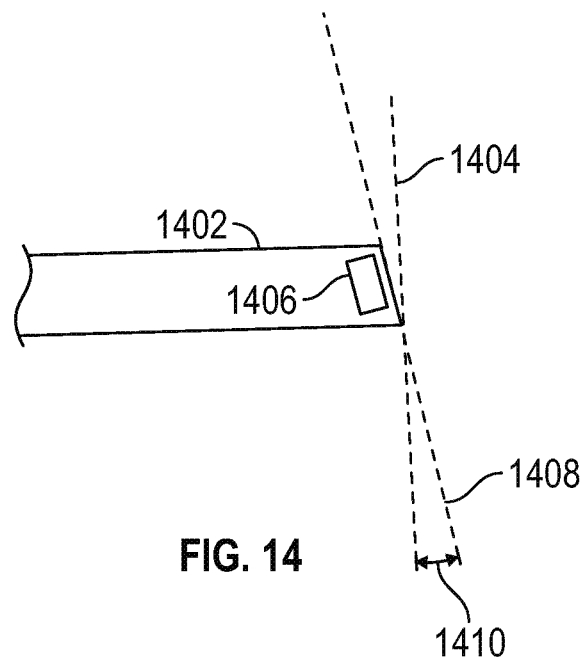
FIG. 14 is a schematic view of the sheath of FIG. 13 having an aperture configured to remove that portion of the sheath tip which would otherwise interfere with the field of view of the camera configured at a "looking up" angle with respect to the sheath axis, such that the aperture defines a plane substantially orthogonal to the camera line of sight in accordance with various embodiments.

FIG. 14 is a schematic view of the sheath of FIG. 13 having an aperture formed by a first cut-away disposed at an angle 1410 (parallel to a plane 1408) with respect to a vertical plane 1404. The value of the angle 1408 is generally analogous to the angle 1310, such that a camera 1406 provides an unobstructed view out the aperture. In this way, the first cut-away is configured to remove that portion of the sheath tip which would otherwise interfere with the field of view of the camera.

Figure 15:
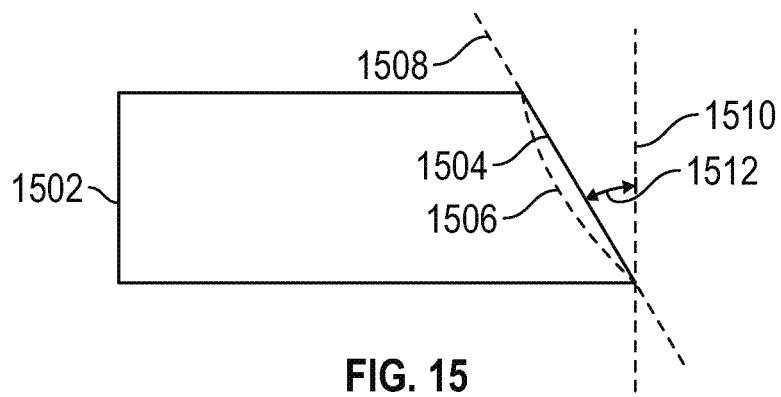
FIG. 15 is a schematic view of a sheath having a distal tip configured with a primary cut-away to facilitate a substantially unobstructed view of the fluid pressure bubble surrounding the surgical site in accordance with various embodiments.

FIG. 15 is a schematic view of a sheath having a distal tip configured with a primary cut-away to facilitate a substantially unobstructed view of the fluid pressure bubble surrounding the surgical site in accordance with various embodiments. In particular, a sheath 1502 includes a primary (or first) cut-away 1504 disposed along a line 1508 inclined an angle 1512 with respect to a vertical plane 1510. Alternatively, the primary cut-away may comprise a concave surface 1506. The value of the angle 1512 generally corresponds to the angles 1310 and 1498, described above.

Figure 16:
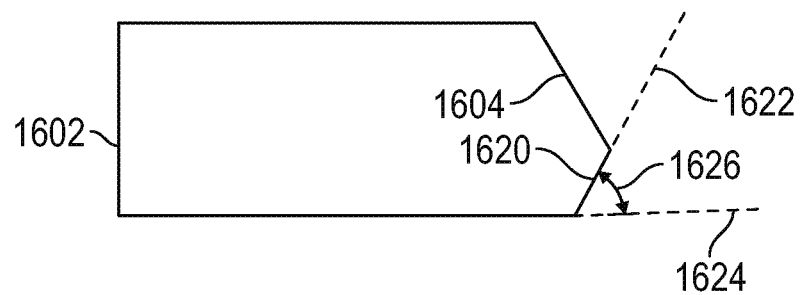
FIG. 16 is a schematic view of the sheath of FIG. 15, further including a secondary cut-away to facilitate stable transient placement ("docking") of the sheath on an anatomical surface in accordance with various embodiments.

FIG. 16 is a schematic view of the sheath of FIG. 15, further including a secondary cut-away to facilitate stable transient placement ("docking") of the sheath on an anatomical surface (e.g., a transverse process) in accordance with various embodiments. In particular, a sheath 1602 includes a primary cut-away 1604 and a secondary cut-away 1620 disposed along a line 1622 inclined at an angle 1626 with respect to a horizontal line 1624 parallel to the longitudinal axis of the sheath. The angle 1626 generally corresponds to the angle at which the DVR assembly is inserted into the patient, typically in the range of 45 to 75 degrees relative to a horizontal plane, and preferable about 60 degrees from a horizontal plane (about 30 degrees from a vertical plane).

Figure 17:
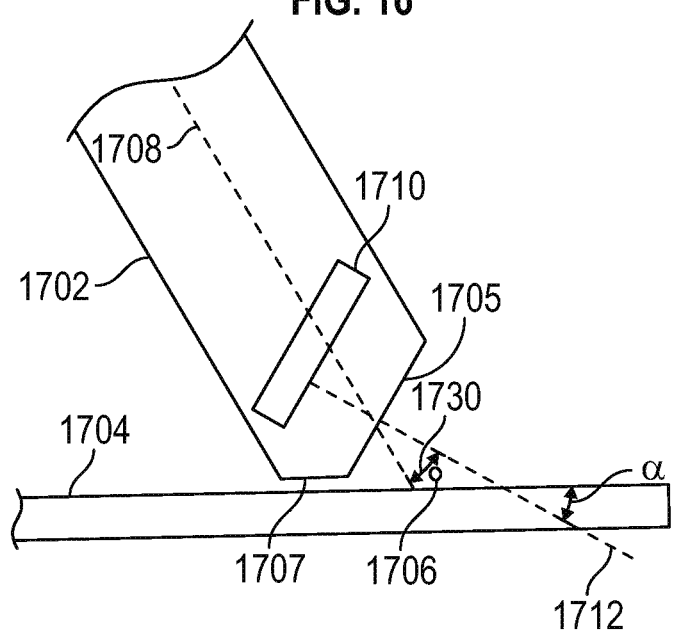
FIG. 17 is a schematic view of the sheath of FIG. 15 in the docked position on a transverse process proximate a cross section view of a medial branch in accordance with various embodiments.

FIG. 17 is a schematic view of the sheath of FIG. 16 in the docked position on a transverse process 1704 proximate a cross section view of a medial branch 1706 in accordance with various embodiments. In particular, a sheath 1702 has a longitudinal axis 1708, a first cut-away 1705, and a second cut-away 1707 generally corresponding to the first and second (primary and secondary) cut-aways, respectively, described above in conjunction with FIG. 16. Also shown in FIG. 17 is an endoscope camera 1710, having a line of sight 1712 suitably inclined at an angle 1730 (e.g., 30 degrees) relative to the axis 1708. As such, the camera remains generally parallel to the aperture defined by the primary cut-away 1705, and maintains an appropriate angle (e.g., 30 degrees) relative to the sheath axis. Consequently, when the surgeon inserts the endoscope assemble into the patient at 60 degrees from a horizontal plane (30 degrees from a vertical planeo, as is typical, the surface 1707 of the sheath may be conveniently stabilized on the (substantially horizontal) surface 1704 of the transverse process.

Figure 18:
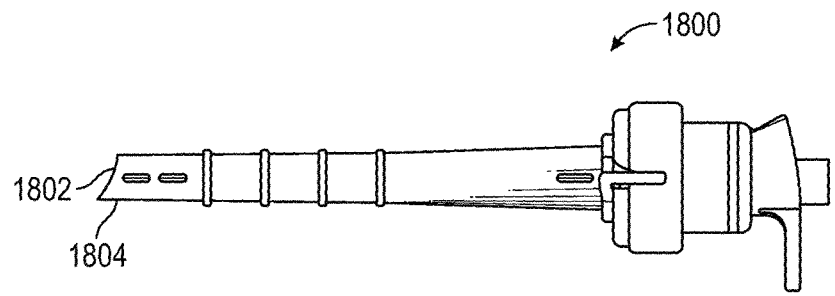
FIG. 18 is a side view of an alternate exemplary sheath illustrating respective first and second cut-away regions in accordance with various embodiments.

FIG. 18 is a side view of an alternate exemplary sheath 1800 illustrating a first cut-away region 1802 and a second cut-away region 1804 in accordance with an alternate embodiment.

Figure 19:
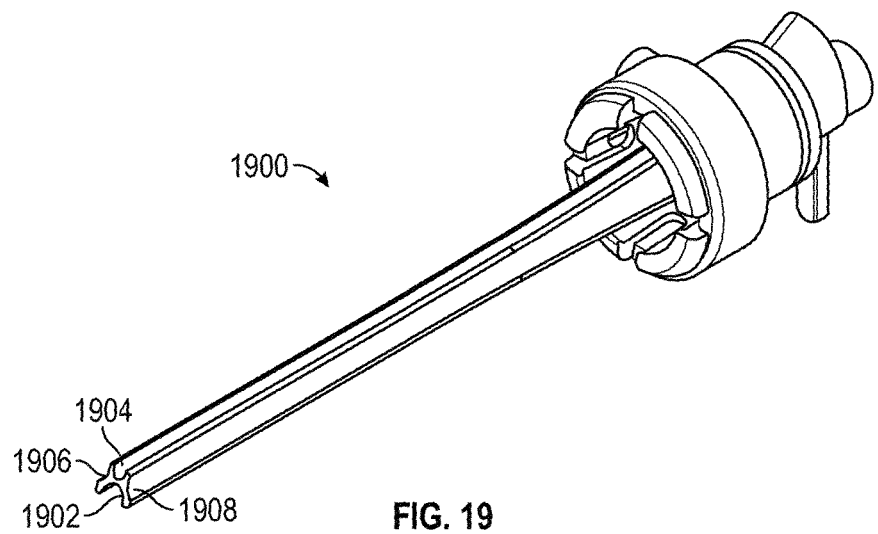
FIG. 19 is a perspective view of a ribbed cannula structure defining an endoscope channel, an electrode channel, a fluid ingress channel, and a fluid egress channel, one or more of which may be configured to be bounded by the inner perimeter of the sheath (not shown in FIGS. 18 and 19) in accordance with various embodiments.

FIG. 19 is a perspective view of a ribbed cannula structure 1900 defining an endoscope channel 1902, an electrode channel 1904, a fluid ingress channel 1906, and a fluid egress channel 1908, one or more of which may be configured to be bounded by the inner perimeter of the sheath (not shown in FIG. 19) in accordance with various embodiments. By using the inner wall of the sheath as a partial boundary of the fluid ingress and egress channels, the total cross sectional area of the sheath may be reduced while still providing adequate cross sectional area for irrigation.

Figure 20:
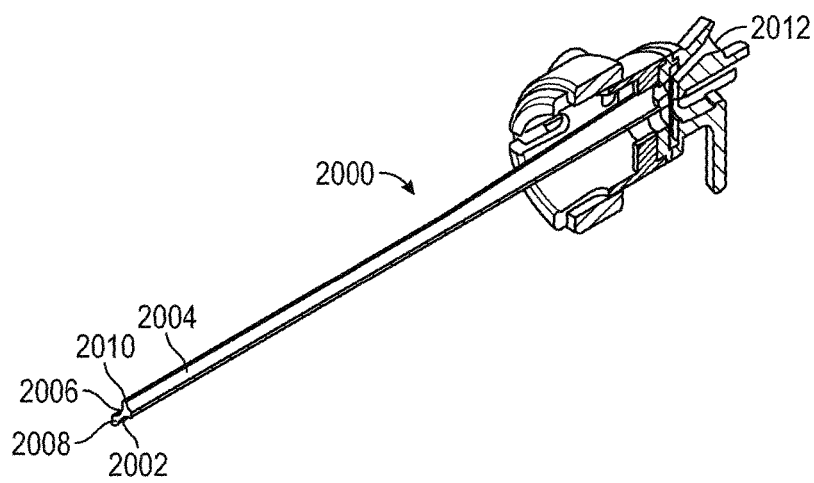
FIG. 20 is a partial section view of the cannula of FIG. 19, with a portion of the cannula structure removed to reveal details associated with the electrode receiving mechanism in accordance with various embodiments.

FIG. 20 is a partial section view of the cannula of FIG. 19, with a portion of the cannula structure removed to reveal details associated with the electrode receiving mechanism in accordance with various embodiments. More particularly, a cannula structure 2000 includes an endoscope channel 2002 (partially removed), a fluid ingress channel 2006, an electrode channel 2004 (partially removed, and an electrode intake chute 2012 configured to allow the surgeon to manually insert the electrode into the electrode channel 2004. In the illustrated embodiment, the cannula structure 200 includes respective lobes 2008, 2010 having convex radii configured to mate with the inner perimeter of the sheath wall to form a fluid seal bounding the fluid ingress channel 2006.

Figure 21:
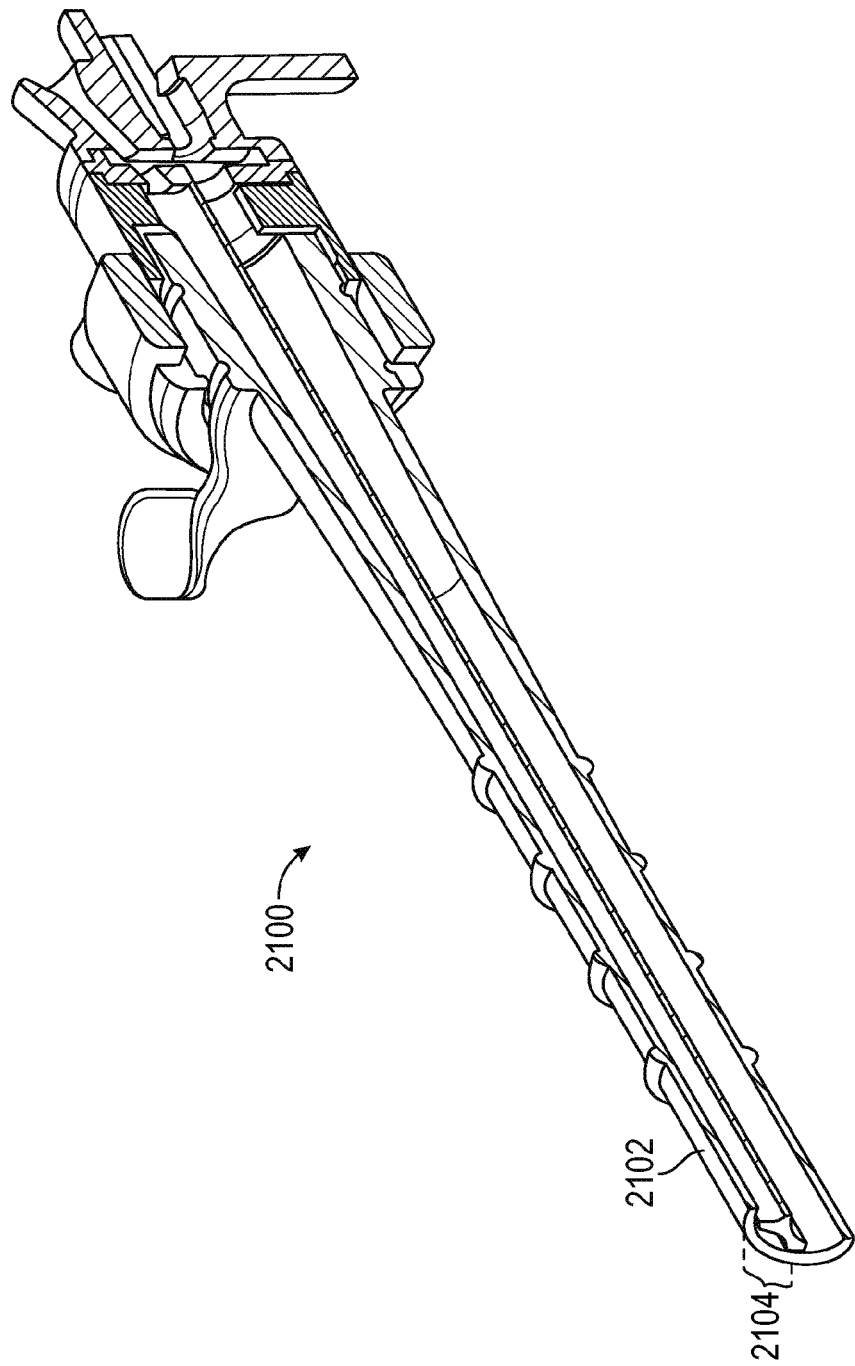
FIG. 21 is a partial section view of the ribbed cannula structure of FIG. 20 illustrating the fluid ingress channel bounded by a portion of the sheath in accordance with various embodiments.

FIG. 21 is a partial section view of the ribbed cannula structure 2100, illustrating the fluid ingress channel bounded by an arc segment 2104 of sheath 2102.

Various configurations for arranging the aforementioned channels within the sheath will now be described in conjunction with FIGS. 22-25. Although the illustrated embodiments depict a sheath having a circular cross section (for example, taken along line IX-IX of FIG. 9), it will be appreciated that the present invention contemplates a sheath having any cross-sectional shape including circular, elliptical, tear drop, and the like. Moreover, while the endoscope and electrode channels are illustrated as having a circular cross section, it will be understood that the invention contemplates endoscopes, electrodes, and/or their associated channels of any suitable cross-sectional shape, size, and configuration.

FIG. 22 is schematic cross-section view of a DVR assembly 2220 including a cannula 2200 coaxially disposed within a sheath 2202, the sheath having an inner perimeter 2203 and an outer perimeter 2205. The cannula 2200 comprises discrete channels, each completely bounded by the cannula structure and defining: i) an electrode channel 2204 having an electrode 2206 received therein; ii) an endoscope channel 2212 having an endoscope 2214 received therein; iii) a fluid ingress channel 2208; and iv) a fluid egress channel 2210. In the illustrated embodiment, the electrode has an outer diameter (OD) in the range of 2.5 millimeters (mm), and the endoscope has an OD in the range of 4 mm.

The present inventor has determined that using wholly contained circular channels for the irrigation channels unnecessarily increases the overall cross-sectional area of the DVR assembly, and therefore proposes various alternate embodiments comprising non-circular irrigation channels to reduce the overall cross-sectional area of the device, while maintaining adequate fluid flow. Indeed, the present inventor has further determined that by providing a fluid egress channel with sufficient cross-sectional area, supplemental suction may be eliminated entirely; that is, the pressure of the fluid ingress channel is sufficient to urge the fluid back through the device and out of the system.

Referring now to FIG. 23, a DVR assembly 2320 includes a sheath 2302 surrounding a cannula 2304, the cannula defining an electrode channel partially intersecting an endoscope channel 2308, both of which are structurally (and, hence, hydraulically) isolated from respective fluid ingress and egress channels 2310 and 2312. Note that the non-circular fluid ingress and egress channels are configured to efficiently utilize the cross sectional within the inner perimeter of the sheath which is not occupied by the electrode and endoscope channels.

FIG. 24 depicts a DVR assembly 2420 including a sheath 2402 surrounding a cannula, the cannula comprising a first partition 2406 defining a fluid ingress channel 2422, and a second partition 2408 defining a fluid egress channel 2420. In the illustrated embodiment, the fluid channel is partially bounded by a cannula partition, and partially bounded by a segment of the inner sheath wall, for example an arc segment 2414 extending between lines 2410 and 2412. To provide hydraulic isolation, each cannula partition may include one or more extensions which contact the sheath, such as regions 2416 and 2418 which substantially seal the fluid channel.

FIG. 25 is schematic cross-section view of a DVR assembly 2520 including a sheath 2502 surrounding a cannula which includes an electrode guide 2508, an endoscope guide 2510, and a common guide 2512. Together, the three guides, the endoscope, the electrode, and the inner sheath wall define a fluid ingress channel 2504 and a fluid egress channel 2506.

FIG. 26 is a perspective view of a DVR device including external fluid ingress and egress connections 2602, 2604 to the aforementioned irrigation channels. Note that the fluid connections and the irrigation channels may be configured for use either with or without supplemental suction.

FIG. 27 is perspective view of a dilator 2702 standing alone, and the dilator 2702 inserted into a sheath 2704. FIG. 27 further depicts the sheath 2704 with the dilator removed, and replaced by a cannula 2708 having an endoscope 2706 and an electrode 2710 inserted therein.

FIG. 28 is a perspective exploded view of a DVR assembly 2800 in accordance with various embodiments. In particular, the DVR 2800 comprises an endoscope including an endoscope handle 2818, an endoscope shaft 2810, and an endoscope camera 2822 mounted to the distal end of the shaft. DVR 2800 further includes a cannula assembly including a cannula top cap 2802, a septum seal 2804, and a ribbed cannula shaft 2806 defining channels for the endoscope, electrode, and irrigation. As described above, once the dilator 2808 us used to guide the sheath into place proximate the transverse process, the dilator is removed and the cannula in inserted into the sheath. In the illustrated embodiment, the cannula assembly may be secured within the sheath 2816 using an outer cover 2810, a wiper seal 2812, and an elastomer spring 2814. The manner in which the spring functions to controllably extend and retract the camera is described in greater detail below in conjunction with FIGS. 29-31.

FIG. 29 is a schematic view of a spring actuated camera assembly 2900 comprising a sheath 2912 having a primary cut-away 2918 and a secondary cut-away 2920 disposed proximate a twig 2916 on the surface of a transverse process 2914. A thumb mount 2902 is connected to an endoscope 2908, and an opposing forefinger mount 2904 is connected to the sheath. A spring 2906 is disposed between the thumb and forefinger mounts, such that urging them toward one another extends the camera 2910 downwardly along the sheath to obtain a close-up view of the twig.

FIG. 30 is a schematic view of the spring actuated camera assembly of FIG. 29, showing the camera 3010 in an extended position closer to the twig 3016 as a result of squeezing the trigger 3002 and thereby compressing the spring. Releasing the trigger 3002 returns the camera to the retracted position shown in FIG. 29, due to the resiliently deformable character of the spring.

FIG. 31 is a schematic view showing both the retracted 3102 and extended 3104 camera positions within the sheath 3112, with the two positions separated by a distance 3106 in the range of 0.1 to 100 mm, and preferably between 0.5 and 10 mm, and most preferably about 2 to 3 mm.

FIG. 32 is a perspective view of an alternative embodiment of a dilator 3200 having a chisel configured 3202 to scrape the transverse process or other anatomical surface to provide a secure footing during a DVR or other procedure. More particularly, as shown in FIGS. 33 and 34, the chisel 3202 comprises a concave scraping blade 3404 extending between respective pointed prongs 3303, 3305. During a DVR procedure, the chisel end 3202 may be used to facilitate insertion of the dilator through the patient's skin. Once the dilator is guided into a position proximate the transverse process, the chisel may used to scrape a small region on the transverse process to thereby provide a secure footing for the sheath to rest upon after the dilator is removed from the sheath and replace by the cannula, as described above.

While the present invention has been described in the context of a DVR procedure in which the device is place proximate the transverse process to facilitate cutting the twig, it will be appreciated that the invention is not so limited. For example, the size, shape, configuration, and relative positions of the sheath, cannula, resiliently deformable spring material and other components may be varied to accommodate virtually any procedure in which it is desirable to place the distal end of the sheath on any anatomical surface to stabilize the device during an endoscopic procedure. Moreover, although a coagulating electrode has been described, it will be understood that any mechanism including mechanical (scissors, knife), thermal (resistive heating element), or optical (e.g., a laser) components may be employed within the scope of the present invention.

An elongated tubular sheath is thus provided for use in endoscopic surgery. The sheath includes: a proximal end configured to removably receive a cannula; a distal end; a horizontal shaft having a longitudinal axis extending between the proximal end and the distal end; a first cut-away generally defining a first plane at the distal end, the first cut-away characterized by a first angle relative to a vertical plane; and a second cut-away generally defining a second plane at the distal end, the second cut-away characterized by a second angle relative to a horizontal plane; wherein the first cut-away has a substantially greater surface area than the second cut-away.

In an embodiment, the first cut-away comprises an aperture for an endoscope camera, and the second cut-away comprises a seat for resting the sheath on an anatomical structure.

In an embodiment, the first angle has a value in the range of 15 to 45 degrees, and preferably approximately 30 degrees.

In an embodiment, the second angle has a value in the range of 15 to 45 degrees, and preferably approximately 30 degrees.

In an embodiment, one or both of the first and second cut-aways form a concavity when viewed from outside the sheath.

In an embodiment, the first cut-away intersects the second cut-away at a third angle in the range of 90 to 150 degrees, and preferably about 90 degrees.

In an embodiment, the sheath further includes an endoscope camera disposed at the distal end, the camera having a line of sight substantially orthogonal to the first plane.

In an embodiment, the sheath further includes a radiolucent marking proximate the distal end.

In an embodiment, the sheath further includes two prongs disposed at an intersection between the first and second planes.

A method of manufacturing a sheath for use in endoscopic surgery is also provided. The method includes: providing a horizontal shaft having a longitudinal axis extending between a proximal end and a distal end; forming a first surface at the distal end, the first surface characterized by a first angle relative to a vertical plane; and forming a second surface at the distal end, the second surface characterized by a second angle relative to a horizontal plane; wherein the first and second angles are in the range of about 30 degrees, and the first surface has a substantially greater surface area than the second surface.

A method is also provided for stabilizing an endoscopic assembly on an internal anatomical surface during surgery. The method includes: providing a tubular sheath having an axis and a distal end, the distal end including a first surface defining an aperture and a second surface defining a docking land, the first and second surfaces each inclined relative to the axis at respective angles in the range of about 45 to 75 degrees; inserting the distal end of the sheath into a patient; inserting an endoscope into the sheath and disposing an endoscope camera proximate the aperture; displaying a signal received from the camera on a screen; and using the displayed signal to maneuver the docking land onto the anatomical surface.

In an embodiment, the method further includes: equipping the endoscopic assembly with an actuator; and manipulating the actuator to move the camera a predetermined distance from a retracted position to an extended position while the docking land is disposed on the anatomical surface.

In an embodiment, the actuator comprises a spring, wherein manipulating the actuator comprises squeezing the trigger to compress the spring.

In an embodiment, moving the camera to the extended position causes the displayed signal to provide a close-up view of the anatomical surface.

In an embodiment, the method further includes: inserting a cutter into the endoscopic assembly; and using the cutter to sever tissue on the anatomical surface while the docking land rests on the anatomical surface.

In an embodiment, the cutter comprises an electrode, the anatomical surface comprises a transverse process of a vertebral body, and the tissue comprises a medial branch of a spinal nerve root, and further wherein severing the tissue comprises extending the electrode beyond the distal end of the sheath to thereby cauterize the medial branch.

In an embodiment, the predetermined distance is in the range of 0.5 to 10 millimeters, and preferably about 2 to 3 millimeters.

An apparatus is also provided for performing endoscopic surgery. The apparatus include: an endoscope of the type including a camera disposed at a distal end of an endoscope shaft; a tubular sheath having a longitudinal axis and configured to slidably receive the endoscope therein such that the camera is disposed proximate a distal end of the sheath; and an actuator configured to toggle the camera between a predetermined retracted position and a predetermined extended position along the sheath axis.

In an embodiment, the actuator includes a trigger configured to be squeezed between a user's thumb and forefinger.

In an embodiment, the trigger includes a first surface connected to the endoscope and a second surface connected to the sheath, such that urging the first surface relative to the second surface causes the camera to move relative to the sheath.

In an embodiment, the distance between the predetermined retracted position and the predetermined extended position is in the range of about 0.5 to 10 millimeters, and preferably about 2 to 3 millimeters.

In an embodiment, the distal end of the sheath includes an aperture substantially parallel to the camera line of sight and a surface configured to facilitate docking the sheath on an anatomical surface.

In an embodiment, the apparatus further includes a spring configured to resiliently deform in response to actuation of the actuator.

In an embodiment, the spring comprises an elastomeric annulus.

In an embodiment, the spring is disposed between the sheath and a handle portion of the endoscope.

A cannula is also provided for use in an endoscopic surgical apparatus of the type including a tubular sheath having an inner wall. The cannula includes: a first channel configured to receive an endoscope shaft; a fluid ingress channel; and a fluid egress channel; wherein at least one of the fluid ingress and fluid egress channels comprise a non-circular cross section.

In an embodiment, the cannula is configured such that, when the cannula is received within the sheath, a portion of one of the fluid ingress and fluid egress channels is bounded by the inner wall.

In an embodiment, the cannula is configured such that, when the cannula is received within the sheath, a portion of the fluid ingress channel and a portion of the fluid egress channel is bounded by the inner wall.

In an embodiment, both the fluid ingress and fluid egress channels comprise a non-circular cross section.

In an embodiment, the cannula further includes a second channel configured to receive an elongated cutter.

In an embodiment, the first and second channels partially intersect.

In an embodiment, a portion of one of first and second channels is bounded by the inner wall.

A cannula is also provided for use in an endoscopic surgical apparatus of the type including a tubular sheath having an inner wall. The cannula includes: a first channel configured to receive an endoscope shaft; a second channel configured to receive an elongated cutter; a third channel configured for fluid ingress; and a fourth channel configured for fluid egress; wherein a portion of each of the first, second, third, and fourth channels is bounded by the inner wall.

In an embodiment, at least one of the third and fourth channels comprise a non-circular cross section, and wherein the cross sectional area of the fourth channel is greater than the cross sectional area of the third channel.

In an embodiment, the cross sectional area of the fourth channel is sufficient to permit fluid egress without supplemental suction.

In a surgical apparatus including a cannula and a surrounding sheath, the sheath having an internal perimeter defining a total cross sectional area, and the cannula comprising a first channel having a first cross-sectional area for receiving an endoscope and a second channel having a second cross-sectional area for receiving a cutting element, a method is provided for configuring a remaining cross sectional area for fluid ingress and fluid egress. The method includes the steps of: determining a value for the remaining cross sectional area by subtracting the first cross sectional area and the second cross sectional area from the total cross sectional area; and determining, using a computer: i) a fluid ingress cross sectional shape having a corresponding fluid ingress cross sectional area; ii) a fluid egress cross-sectional shape having a corresponding fluid egress cross sectional area; and iii) a cannula cross sectional shape having a corresponding cannula cross sectional area; wherein the remaining cross sectional area equals the sum of the fluid ingress cross sectional area, the fluid egress cross sectional area, and the cannula cross sectional area.

In an embodiment, determining the cannula cross-sectional shape, the fluid ingress cross-sectional shape, and the fluid egress cross-sectional shape involves: first determining at least one of the fluid ingress and fluid egress cross-sectional shapes, and thereafter determining the cannula cross-sectional shape based on the previously determined at least one of the fluid ingress and fluid egress cross-sectional shapes.

In an embodiment, determining the cannula cross-sectional shape, the fluid ingress cross-sectional shape, and the fluid egress cross-sectional shape involves: first determining the cannula cross-sectional shape, and thereafter determining at least one of the fluid ingress and fluid egress cross-sectional shapes based on the previously determined cannula cross-sectional shape.

In an embodiment, at least one of the fluid ingress and fluid egress cross sectional shapes are non-circular.

In an embodiment, at least one of the fluid ingress and fluid egress cross sectional areas are partially bounded by the cannula and partially bounded by the sheath internal perimeter.

In an embodiment, the fluid egress cross sectional area is greater than the fluid ingress cross sectional area.

In an embodiment, the cannula includes: respective first and second segments configured for sliding contact with the sheath internal perimeter and defining therebetween a region of the fluid ingress cross sectional area which is bounded by the sheath internal perimeter; and respective third and fourth segments configured for sliding contact with the sheath internal perimeter and defining therebetween a region of the fluid egress cross sectional area which is bounded by the sheath internal perimeter.

In an embodiment, the cannula shape comprises a FIG. 8.

In an embodiment, the sheath internal perimeter comprises a circular cross section.

In an embodiment, the sheath internal perimeter comprises a non-circular cross section.

An endoscopic surgical apparatus includes an endoscope having a camera disposed at a distal end of an endoscope shaft, the camera characterized by a line of sight tilted upwardly by a tilt angle relative to the shaft. The apparatus further includes an elongated tubular sheath comprising: a proximal end configured to removably receive the endoscope shaft; a distal end; a horizontal tubular sheath shaft portion having a longitudinal axis extending between the proximal end and the distal end; and an aperture substantially orthogonal to the camera line of sight.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. An apparatus for performing endoscopic surgery, comprising:
   an endoscope including a camera disposed at a distal end of an endoscope shaft;
   a tubular sheath having a longitudinal axis and configured to slidably receive the endoscope therein such that the camera is disposed proximate a distal end of the sheath; and
   an axially translating actuator configured to selectively position the camera relative to the distal end of the sheath between a retracted position and an extended position along the sheath axis;
   wherein the distal end of the sheath comprises:
   a camera aperture inclined at a first angle relative to the sheath axis; and
   a substantially flat docking surface inclined at a second angle relative to the sheath axis in a direction different from the aperture.

2. The apparatus of claim 1, wherein the actuator comprises a trigger configured to be squeezed between a user's thumb and forefinger.

3. The apparatus of claim 2, wherein the trigger comprises a first surface connected to the endoscope and a second surface connected to the sheath, such that urging the first surface relative to the second surface causes the camera to move relative to the sheath.

4. The apparatus of claim 3, wherein the distance between the predetermined retracted position and the predetermined extended position is in the range of about 0.5 to 10 millimeters.

5. The apparatus of claim 3, wherein the distance between the predetermined retracted position and the predetermined extended position is in the range of about 2 to 3 millimeters.

6. The apparatus of claim 3, further comprising a spring configured to resiliently deform in response to actuation of the actuator.

7. The apparatus of claim 6, wherein the spring comprises an elastomeric annulus.

8. The apparatus of claim 7, wherein the spring is disposed between the sheath and a handle portion of the endoscope.

* * * * *